(12) United States Patent
Virca et al.

(10) Patent No.: US 6,387,676 B1
(45) Date of Patent: May 14, 2002

(54) HUMAN CDNAS ENCODING POLYPEPTIDES HAVING KINASE FUNCTIONS

(75) Inventors: G. Duke Virca, Bellevue; Timothy A. Bird, Bainbridge ISland; Dirk M. Anderson; John S. Marken, both of Seattle, all of WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/509,902

(22) PCT Filed: Aug. 3, 1999

(86) PCT No.: PCT/US99/17630

§ 371 Date: Jun. 23, 2000

§ 102(e) Date: Jun. 23, 2000

(87) PCT Pub. No.: WO00/08180

PCT Pub. Date: Feb. 17, 2000

Related U.S. Application Data

(60) Provisional application No. 60/095,270, filed on Aug. 4, 1998, and provisional application No. 60/099,972, filed on Sep. 11, 1998.

(51) Int. Cl.$^7$ .............................. C12N 9/00; C12N 9/12; C12N 1/20; C12N 5/06; C12N 15/00
(52) U.S. Cl. .................... 435/194; 435/183; 435/252.3; 435/255.1; 435/325; 435/419; 435/320.1; 435/348; 536/23.2
(58) Field of Search ................................ 435/183, 194, 435/252.3, 255.1, 419, 325, 320.1, 348; 536/23.2

(56) References Cited

U.S. PATENT DOCUMENTS

| | | | |
|---|---|---|---|
| 6,013,455 A | 1/2000 | Bandman et al. | ............... 435/6 |
| 6,242,947 B1 | 7/2001 | Bandman et al. | |

FOREIGN PATENT DOCUMENTS

| | | |
|---|---|---|
| WO | WO 969/37787 | 7/1999 |
| WO | WO00/73469 A3 | 12/2000 |
| WO | WO00/73469 A2 | 12/2000 |

OTHER PUBLICATIONS

Deak et al., *EMBO J* 17(15): 4426–4441, Aug. 3, 1998.
Marra et al., EMBL Database Accession No. AA472165, Jun. 1997.
Pierrat et al., *J Biol Chem* 273(45): 29662–29671, Nov. 6, 1998.
Deak et al. (References 1 and 2), GenBank Accession No. AF074393, May 28, 1999.
Deak et al . (References 1 and 2), GenBank Accession No. AF074715, Oct. 24, 1998.
Lesslauer, (Reference 1) and Pierrat et al. (Reference 2), GenBank Accession No. AJ010119, Nov. 11, 1998.
Hillman et al., GeneSeq Accession No. Y76749, Apr. 17, 2000.
Hillman et al., GeneSeq Accession No. Z86793, Apr. 17, 2000.
Flanagan and Plowman, GeneSeq Accession No. X87397, Oct. 8, 1999.
Flanagan and Plowman, GeneSeq Accession No. Y06527, Oct. 8, 1999.
Hori et al., *Oncogene* 19(27): 3101–3109, Jun. 2000.
Hori et al. (Reference 1) and Hori (Reference 2), GenBank Accession No. AF207547, Jul. 1, 2000.

*Primary Examiner*—Rebecca E. Prouty
*Assistant Examiner*—Manjunath N. Rao
(74) *Attorney, Agent, or Firm*—Suzanne A. Sprunger

(57) ABSTRACT

The invention is directed to purified and isolated human polypeptides having kinase function, the nucleic acids encoding such polypeptides, processes for production of recombinant forms of such polypeptides, antibodies generated against these polypeptides, fragmented peptides derived from these polypeptides, the use of such polypeptides and fragmented peptides in phosphorylation reactions and as molecular weight markers, the use of such polypeptides and fragmented peptides as controls for peptide fragmentation, the use of such polypeptides in screening assays, and kits comprising these reagents.

24 Claims, No Drawings

HUMAN CDNAS ENCODING POLYPEPTIDES HAVING KINASE FUNCTIONS

CROSS-REFERENCE TO RELATED APPLICATIONS

This application is a national application under 35 U.S.C. § 371 of International Application No. PCT/US99/17630, having an international filing date of Aug. 3, 1999; which claims the priority of provisional applications U.S. Ser. No. 60/095,270, filed Aug. 4, 1998, and U.S. Ser. No. 60/099,972, filed Sep. 11, 1998; all of which are incorporated by reference herein.

FIELD OF THE INVENTION

The invention is directed to purified and isolated human polypeptides having kinase function, the nucleic acids encoding such polypeptides, processes for production of recombinant forms of such polypeptides, antibodies generated against these polypeptides, fragmented peptides derived from these polypeptides, the use of such polypeptides and fragmented peptides in phosphorylation reactions and as molecular weight markers, the use of such polypeptides and fragmented peptides as controls for peptide fragmentation, the use of such polypeptides in screening assays, and kits comprising these reagents.

BACKGROUND OF THE INVENTION

The eukaryotic protein kinases make up a large and rapidly expanding family of proteins related on the basis of homologous catalytic domains. Spurred by the development of gene cloning and sequencing methodologies, distinct protein kinase genes have been identified from a wide selection of invertebrates and lower eukaryotes, including Drosophila, Caenorhabditis elegans, Aplysia, Hydra, Dictyostelium, and budding (Saccharomyces cerevisiae) and fission (Schizosaccharomyces pombe) yeast. Homologous genes have also been identified in higher plants. Protein kinases, however, are not limited to the eukaryotes. Enzyme activities have been well documented in prokaryotes, but the prokaryotic protein kinase genes are not obviously homologous to those of the eukaryotes. Because protein kinases are useful biochemical reagents, there is a need in the art for the continued discovery of unique members of the protein kinase family.

In addition, the discovery and identification of proteins are at the forefront of modern molecular biology and biochemistry. The identification of the primary structure, or sequence, of a sample protein is the culmination of an arduous process of experimentation. In order to identify an unknown sample protein, the investigator can rely upon comparison of the unknown sample protein to known peptides using a variety of techniques known to those skilled in the art. For instance, proteins are routinely analyzed using techniques such as electrophoresis, sedimentation, chromatography, and mass spectrometry.

Comparison of an unknown protein sample to polypeptides of known molecular weight allows a determination of the apparent molecular weight of the unknown protein sample (T. D. Brock and M. T. Madigan, Biology of Microorganisms 76–77 (Prentice Hall, 6d ed. 1991)). Protein molecular weight standards are commercially available to assist in the estimation of molecular weights of unknown protein samples (New England Biolabs Inc. Catalog:130–131, 1995; J. L. Hartley, U.S. Pat. No. 5,449,758). However, the molecular weight standards may not correspond closely enough in size to the unknown sample protein to allow an accurate estimation of apparent molecular weight.

The difficulty in estimation of molecular weight is compounded in the case of proteins that are subjected to fragmentation by chemical or enzymatic means (A. L. Lehninger, Biochemistry 106–108 (Worth Books, 2d ed. 1981)). Chemical fragmentation can be achieved by incubation of a protein with a chemical, such as cyanogen bromide, which leads to cleavage of the peptide bond on the carboxyl side of methionine residues (E. Gross, Methods in Enz. 11:238–255, 1967). Enzymatic fragmentation of a protein can be achieved by incubation of a protein with a protease that cleaves at multiple amino acid residues (D. W. Cleveland et al., J. Biol. Chem. 252:1102–1106, 1977). Enzymatic fragmentation of a protein can also be achieved by incubation of a protein with a protease, such as Achromobacter protease I (F. Sakiyama and A. Nakata, U.S. Pat. No. 5,248,599; T. Masaki et al., Biochim. Biophys. Acta 660:44–50, 1981; T. Masaki et al., Biochim. Biophys. Acta 660:51–55, 1981), which leads to cleavage of the peptide bond on the carboxyl side of lysine residues. The molecular weights of the fragmented peptides can cover a large range of molecular weights and the peptides can be numerous. Variations in the degree of fragmentation can also be accomplished (D. W. Cleveland et al., J. Biol. Chem. 252:1102–1106, 1977).

The unique nature of the composition of a protein with regard to its specific amino acid constituents results in a unique positioning of cleavage sites within the protein. Specific fragmentation of a protein by chemical or enzymatic cleavage results in a unique "peptide fingerprint" (D. W. Cleveland et al., J. Biol. Chem. 252:1102–1106, 1977; M. Brown et al., J. Gen. Virol. 50:309–316, 1980). Consequently, cleavage at specific sites results in reproducible fragmentation of a given protein into peptides of precise molecular weights. Furthermore, these peptides possess unique charge characteristics that determine the isoelectric pH of the peptide. These unique characteristics can be exploited using a variety of electrophoretic and other techniques (T. D. Brock and M. T. Madigan, Biology of Microorganisms 76–77 (Prentice Hall, 6d ed. 1991)).

When a peptide fingerprint of an unknown protein is obtained, this can be compared to a database of known proteins to assist in the identification of the unknown protein (W. J. Henzel et al., Proc. Natl. Acad. Sci. USA 90:5011–5015, 1993; B. Thiede et al., Electrophoresis 1996, 17:588–599, 1996). A variety of computer software programs are accessible via the Internet to the skilled artisan for the facilitation of such comparisons, such as MultiIdent (Internet site: www.expasy.ch/sprot/multiident.html), PeptideSearch (Internet site: www.mann.emblheiedelberg.de...deSearch/FR__PeptideSearchForm.html), and ProFound (Internet site:www.chait-sgi.rockefeller.edu/cgi-bin/prot-id-frag.html). These programs allow the user to specify the cleavage agent and the molecular weights of the fragmented peptides within a designated tolerance. The programs compare these molecular weights to protein databases to assist in the elucidation of the identity of the sample protein. Accurate information concerning the number of fragmented peptides and the precise molecular weight of those peptides is required for accurate identification. Therefore, increasing the accuracy in the determination of the number of fragmented peptides and the precise molecular weight of those peptides should result in enhanced success in the identification of unknown proteins.

Fragmentation of proteins is further employed for the production of fragments for amino acid composition analysis and protein sequencing (P. Matsudiara, *J. Biol. Chem.* 262:10035–10038, 1987; C. Eckerskom et al., *Electrophoresis* 1988, 9:830–838, 1988), particularly the production of fragments from proteins with a "blocked" N-terminus. In addition, fragmentation of proteins can be used in the preparation of peptides for mass spectrometry (W. J. Henzel et al., *Proc. Natl. Acad Sci. USA* 90:5011–5015, 1993; B. Thiede et al., *Electrophoresis* 1996, 17:588–599, 1996), for immunization, for affinity selection (R. A. Brown, U.S. Pat. No. 5,151,412), for determination of modification sites (e.g. phosphorylation), for generation of active biological compounds (T. D. Brock and M. T. Madigan, *Biology ofMicroorganisms* 300–301 (Prentice Hall, 6d ed. 1991)), and for differentiation of homologous proteins (M. Brown et al., *J. Gen. Virol.* 50:309–316, 1980).

In view of the continuing interest in protein research and the elucidation of protein structure and properties, there exists a need in the art for polypeptides having kinase function or suitable for use in peptide fragmentation studies and in molecular weight measurements.

SUMMARY OF THE INVENTION

The invention aids in fulfilling these needs in the art. The invention encompasses an isolated human nucleic acid molecule comprising the DNA sequence of SEQ ID NO:1, 2, 3, 4, 5, 6, 13, or 15 and an isolated human nucleic acid molecule encoding the amino acid sequence of SEQ ID NO:7, 8, 9, 10, 11, 12, 14, or 16. The invention also encompasses nucleic acid molecules complementary to these sequences. As such, the invention includes double-stranded nucleic acid molecules comprising the DNA sequence of SEQ ID NO:1, 2, 3, 4, 5, 6, 13, or 15 and isolated nucleic acid molecules encoding the amino acid sequence of SEQ ID NO:7, 8, 9, 10, 11, 12, 14 or 16. Both single-stranded and double-stranded RNA and DNA nucleic acid molecules are encompassed by the invention. These molecules can be used to detect both single-stranded and double-stranded RNA and DNA variants encompassed by the invention. A double-stranded DNA probe allows the detection of nucleic acid molecules equivalent to either strand of the nucleic acid molecule. Isolated nucleic acid molecules that hybridize to a denatured, double-stranded DNA comprising the DNA sequence of SEQ ID NO:1, 2,3, 4, 5,6, 13, or 15, or an isolated nucleic acid molecule encoding the amino acid sequence of SEQ ID NO:7, 8, 9, 10, 11, 12, 14, or 16 are within the invention. A preferred set of hybridization conditions are those of moderate stringency: in 50% formamide and 6×SSC, at 42° C. with washing conditions of 60° C., 0.5×SSC, 0.1% SDS.

The invention further encompasses isolated nucleic acid molecules derived by in vitro mutagenesis from SEQ ID NO:1, 2, 3, 4, 5, 6, 13, or 15. In vitro mutagenesis would include numerous techniques known in the art including, but not limited to, site-directed mutagenesis, random mutagenesis, and in vitro nucleic acid synthesis. The invention also encompasses isolated nucleic acid molecules degenerate from SEQ ID NO:1, 2, 3, 4, 5, or 6 (and the resulting amino acid sequence) as a result of the genetic code, isolated nucleic acid molecules that are allelic variants of human DNA of the invention, or a species homolog of DNA of the invention. The invention also encompasses recombinant vectors that direct the expression of these nucleic acid molecules and host cells transformed or transfected with these vectors. In addition, the invention encompasses methods of using the nucleic acid noted above in assays to identify chromosomes, map human genes, and study tumors.

The invention also encompasses isolated polypeptides encoded by these nucleic acid molecules, including isolated polypeptides having a molecular weights as determined by SDS-PAGE, isolated polypeptides in non-glycosylated form, and fragments thereof. The invention further includes synthetic polypeptides encoded by these nucleic acid molecules. Peptides and fragments of these polypeptides, however derived, are also part of the invention and may be produced by any standard means, from chemical, enzymatic, recombinant, or synthetic methods. Isolated polyclonal or monoclonal antibodies that bind to these polypeptides are encompassed by the invention. The invention further encompasses methods for the production of polypeptides having kinase functions including culturing a host cell under conditions promoting expression and recovering the polypeptide from the culture medium. Especially, the expression of polypeptides having kinase functions in bacteria, yeast, plant, insect, and animal cells is encompassed by the invention.

In general, the polypeptides of the invention having kinase function can be used to phosphorylate target proteins and to radiolabeled target proteins with $^{32}$P. In addition, the polypeptides of the invention having kinase function can be used to identify proteins having a phosphate activity.

In addition, assays utilizing polypeptides having kinase functions to screen for potential inhibitors of activity associated with polypeptide counter-structure molecules, and methods of using polypeptides having kinase functions as therapeutic agents for the treatment of diseases mediated by polypeptide counter-structure molecules are encompassed by the invention. Methods of using polypeptides having kinase functions in the design of inhibitors thereof are also an aspect of the invention. The invention further encompasses use of polypeptides of the invention to screen for agonists and antagonists.

The invention further encompasses the fragmented peptides produced from polypeptides of the invention by chemical or enzymatic treatment. In addition, the polypeptides of the invention and fragmented peptides thereof, wherein at least one of the sites necessary for fragmentation by chemical or enzymatic means has been mutated, are an aspect of the invention.

The invention further includes a method for using these polypeptides and fragmented peptides thereof as molecular weight markers that allow the estimation of the molecular weight of a protein or a fragmented protein sample. The invention also encompasses a method for the visualization of the molecular weight markers of the invention thereof using electrophoresis. The invention further encompasses methods for using the polypeptides of the invention and fragmented peptides thereof as markers, which aid in the determination of the isoelectric point of a sample protein. The invention also encompasses methods for using polypeptides of the invention and fragmented peptides thereof as controls for establishing the extent of fragmentation of a protein sample.

Further encompassed by this invention are kits to aid the determination of molecular weights of a sample protein utilizing polypeptide molecular weight markers of the invention, fragmented peptides thereof, and forms of these polypeptide molecular weight markers, wherein at least one of the sites necessary for fragmentation by chemical or enzymatic means has been mutated.

DETAILED DESCRIPTION OF THE INVENTION

The protein kinases are a large family of enzymes, many of which mediate the response of eukaryotic cells to external stimuli. In recent years, members of the protein kinase family have been discovered at an accelerated pace. The surge in the number of known protein kinases has been largely due to the advent of gene cloning and sequencing techniques. Amino acid sequences deduced from nucleotide sequences are considered to represent protein kinases if they include certain key residues that are highly conserved in the protein kinase catalytic domain. A cDNA encoding a human polypeptide has been isolated and is set forth in SEQ ID NO:1, 2, 3, 4, 5, 6, 13, or 15. This discovery of the cDNA encoding human polypeptides having kinase functions enables construction of expression vectors comprising nucleic acid sequences encoding polypeptides having kinase functions; host cells transfected or transformed with the expression vectors; biologically active human polypeptides having kinase functions, and molecular weight markers as isolated and purified proteins; and antibodies immunoreactive with polypeptides of the invention.

More particularly, the invention relates to certain nucleotide sequences. A "nucleotide sequence" refers to a polynucleotide molecule in the form of a separate fragment or as a component of a larger nucleic acid construct, that has been derived from DNA or RNA isolated at least once in substantially pure form (i.e., free of contaminating endogenous materials) and in a quantity or concentration enabling identification, manipulation, and recovery of its component nucleotide sequences by standard biochemical methods (such as those outlined in Sambrook et al., *Molecular Cloning: A Laboratory Manual*, 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Particularly preferred nucleotide sequences of the invention include the following:

```
NAME: HH0900-BF04 DNA

Nucleotide sequence:

GTACGCCATGAAGGTGCTGCGCAAGGCGGCGCTGGTGCAGCGCGCCAAGA  (SEQ ID NO:1)

CGCAAGAGCACACGCGCACCGAGCGCTCGGTGCTGGAGCTGGTGCGCCAG

GCGCCCTTCCTGGTCACGCTGCACTACGCTTTCCAGACGGATGCCAAGCT

GCACCTCATCCTGGACTATGTGAGCGGCGGG;

NAME: HH2046-BF04 DNA

Nucleotide sequence:

CCCGAGAGGTGCCACATCAGACCGCCTCCGACTTCGTGCGGGACTCGGCG  (SEQ ID NO:2)

GCCAGCCACCAGGCGGAGCCCGAGGCGTACGAGCGGCGCGTGTGCTTCCT

GCTTCTGCAACTCTGCAACGGGCTGGAGCACCTGAAGGAGCACGGGATCA

TCCACCGGGACCTGTGCCTGGAGAACCTGCTGCTGGTGCACTGCACCCTC

CAGGCCGGCCCCGGGCCCGCC;

Name: JJ503-KS DNA nucleotide sequence

CGGGCAGGGCTGGAGCTGGGCTGGGATCCCGAGCTCGGCAGCAGCGCAGCGGGCCGGCCCACCTGCTGGTGC  (SEQ ID NO:3)

CCTGGAGGCTCTGAGCCCCGGCGGCGCCCGGGCCCACGCGGAACGACGGGGCGAGATGCGAGCCACCCCTCT

GGCTGCTCCTGCGGGTTCCCTGTCCAGGAAGAAGCGGTTGGAGTTGGATGACAACTTAGATACCGAGCGTCC

CGTCCAGAAACGAGCTCGAAGTGGGCCCCAGCCCAGACTGCCCCCCTGCCTGTTGCCCCTGAGCCCACCTAC

TGCTCCAGATCGTGCAACTGCTGTGGCCACTGCCTCCCGTCTTGGGCCCTATGTCCTCCTGGAGCCCGAGGA

GGGCGGGCGGGCCTACCAGGCCCTGCACTGCCCTACAGGCACTGAGTATACCTGCAAGGTGTACCCCGTCCA

GGAAGCCCTGGCCGTGCTGGAGCCCTACGCGCGGCTGCCCCCGCACAAGCATGTGGCTCGGCCCACTGAGGT

CCTGGCTGGTACCCAGCTCCTCTACGCCTTTTTCACTCGGACCCATGGGGACATGCACAGCCTGGTGCGAAG

CCGCCACCGTATCCCTGAGCCTGAGGCTGCCGTGCTCTTCCGCCAGATGGCCACCGCCCTGGCGCACTGTCA

CCAGCACGGTCTGGTCCTGCGTGATCTCAAGCTGTGTCGCTTTGTCTTCGCTGACCGTGAGAGGAAGAAGCT

GGTGCTGGAGAACCTGGAGGACTCCTGCGTGCTGACTGGGCCAGATGATTCCCTGTGGGACAAGCACGCGTG

CCCAGCCTACGTGGGACCTGAGATACTCAGCTCACGGGCCTCATACTCGGGCAAGGCAGCCGATGTCTGGAG
```

-continued

CCTGGGCGTGGCGCTCTTCACCATGCTGGCCGGCCACTACCCCTTCCAGGACTCGGAGCCTGTCCTGCTCTT

CGGCAAGATCCGCCGCGGGGCCTACGCCTTGCCTGCAGGCCTCTCGGCCCCTGCCCGCTGTCTGGTTCGCTG

CCTCCTTCGTCGGGAGCCAGCTGAACGGCTCACAGCCACAGGCATCCTCCTGCACCCCTGGCTGCGACAGGA

CCCGA;

Name: QQ1249-BF04 DNA

Nucleotide sequence:

CAGCGAGAAGCCGACATGCATCGCCTCTTCAATCACCCCAACATCCTTCG (SEQ ID NO:4)

CCTCGTGGCTTACTGTCTGAGGGAACGGGGTGCTAAGCATGAGGCCTGGC

TGCTGCTACCATTCTTCAAGAGAGGTACGCTGTGGAATGAGATAGAAAGG

CTGAAGGACAAAGGCAACTTCCTGACCGAGGATCAAATCCTTTGGCTGCT

GCTGGGGATCTGCAGAGGCCTTGAGGCCATTCATGCCAAGGGTTATGCCT

ACAGAGACTTGAAGCCCACCAATATATTGCTTGGAGATGAGGGGCAGCCA

GTTTTAATGGACTTGGGTTCCATGAATCAAGCATGCATCCATGTGGAGGG

CTCCCGCCAGGCTCTGACCCTGCAGGACTGGGCAGCCC;

Name: QQ3351-BF04 DNA

Nucleotide sequence:

ATGCTAACTAGTTTAAACAGATCTTGGAACGAGACGACCTGCTGTGGAAGAGCGAGCTTTTTGGAACTGTGC (SEQ ID NO:5)

ACGGGACAGATTGGACGCACACCCCTCGGGAGGCGCGAAGGCATGGAAAATTTGAAGCATATTATCACCCTT

GGCCAGGTCATCCACAAACGGTGTGAAGAGATGAAATACTGCAAGAAACAGTGCCGGCGCCTGGGCCACCGC

GTCCTCGGCCTGATCAAGCCTCTGGAGATGCTCCAGGACCAAGGAAAGAGGAGCGTGCCCTCTGAGAAGTTA

ACCACAGCCATGAACCGCTTCAAGGCTGCCCTGGAGGAGGCTAATGGGGAGATAGAAAAGTTCAGCAATAGA

TCCAATATCTGCAGGTTTCTAACAGCAAGCCAGGACAAAATACTCTTCAAGGACGTGAACAGGAAGCTGAGT

GATGTCTGGAAGGAGCTCTCGCTGTTACTTCAGGTTGAGCAACGCATGCCTGTTTCACCCATAAGCCAAGGA

GCGTCCTGGGCACAGGAAGATCAGCAGGATGCAGACGAAGACAGGCGAGCTTTCCAGATGCTAAGAAGAGAT

AATGAAAAAATAGAAGCTTCACTGAGACGATTAGAAATCAACATGAAAGAAATCAAGGAAACTTTGAGGCAG

TATTTACCACCAAAATGCATGCAGGAGATCCCGCAAGAGCAAATCAAGGAGATCAAGAAGGAGCAGCTTTCA

GGATCCCCGTGGATTCTGCTAAGGGAAAATGAAGTCAGCACACTTTATAAAGGAGAATACCACAGAGCTCCA

GTGGCCATAAAAGTATTCAAAAAACTCCAGGCTGGCAGCATTGCAATAGTGAGGCAGACTTTCAATAAGGAG

ATCAAAACCATGAAGAAATTCGAATCTCCCAACATCCTGCGTATATTTGGGATTTGCATTGATGAAACAGTG

ACTCCGCCTCAATTCTCCATTGTCATGGAGTACTGTGAACTCGGGACCCTGAGGGAGCTGTTGGATAGGGAA

AAAGACCTCACACTTGGCAAGCGCATGGTCCTAGTCCTGGGGGCAGCCCGAGGCCTATACCGGCTACACCAT

TCAGAAGCACCTGAACTCCACGGAAAAATCAGAAGCTCAAACTTCCTGGTAACTCAAGGCTACCAAGTGAAG

CTTGCAGGATTTGAGTTGAGGAAAACACAGACTTCCATGAGTTTGGGAACTACGAGAGAAAAGACAGACAGA

GTCAAATCTACAGCATATCTCTCACCTCAGGAACTGGAAGATGTATTTTATCAATATGATGTAAAGTCTGAA

ATATACAGCTTTGGAATCGTCCTCTGGGAAATCGCCACTGGAGATATCCCGTTTCAAGGCTGTAATTCTGAG

AAGATCCGCAAGCTGGTGGCTGTGAAGCGGCAGCAGGAGCCACTGGGTGAAGACTGCCCTTCAGAGCTGCGG

GAGATCATTGATGAGTGCCGGGCAGCAGGTCGTCTCGTTCCAAGATCTGTAGCGGCCGCCCCGGGCCGTCGAC

GTTTAAACGCGTGGCCCTCGAGAGGTTTTCCGATCCGGTCGAT, and

Name: SS1771

Nucleotide sequence:

-continued

CTTCCCGCTG GACGTGGAGT ACGGAGGCCC AGACCGGAGG TGCCCGCCTC (SEQ ID NO:6)

CGCCCTACCC GAAGCACCTG CTGCTGCGCA GCAAGTCGGA GCAGTACGAC

CTGGACAGCC TGTGCGCAGG CATGGAGCAG AGCCTCCGTG CGGGCCCCAA

CGAGCCCGAG GGCGGCGACA AGAGCCGCAA AAGCGCCAAG GGGGACAAAG

GCGGAAAGGA TAAAAAGCAG ATTCAGACCT CTCCCGTTCC CGTCCGCAAA

AACAGCAGAG ACGAAGAGAA GAGAGAGTCA CGCATCAAGA GCTACTCGCC

ATACGCCTTT AAGTTCTTCA TGGAGCAGCA CGTGGAGAAT GTCATCAAAA

CCTACCAGCA GAAGGTTAAC CGGAGGCTGC AGCTGGAGCA AGAAATGGCC

AAAGCTGGAC TCTGTGAAGC TGAGCAGGAG CAGATGCGGA AGATCCTCTA

CCAGAAAGAG TCTAATTACA ACAGGTTAAA GAGGGCCAAG ATGGACAAGT

CTATGTTTGT CAAGATCAAA ACCCTGGGGA TCGGTGCCTT TGGAGAAGTG

TGCCTTGCTT GTAAGGTGGA CACTCACGCC CTGTACGCCA TGAAGACCCT

AAGGAAAAAG GATGTCCTGA ACCGGAATCA GGTGGCCCAC GTCAAGGCCG

AGAGGGACAT CCTGGCCGAG GCAGACAATG AGTGGGTGGT CAAACTCTAC

TACTCCTTCC AAGACAAAGA CAGCCTGTAC TTTGTGATGG ACTACATCCC

TGGTGGGGAC ATGATGAGCC TGCTGATCCG GATGGAGGTC TTCCCTGAGC

ACCTGGCCCG GTTCTACATC GCAGAGCTGA CTTTGGCCAT TGAGAGTGTC

CACAAGATGG GCTTCATCCA CCGAGACATC AAGCCTGATA ACATTTTGAT

AGATCTGGAT GGTCACATTA AACTCACAGA TTTCGGCCTC TGCACTGGGT

TCAGGTGGAC TCACAATTCC AAATATTACC AGAAAGGGAG CCATGTCAGA

CAGGACAGCA TGGAGCCCAG CGACCTCTGG GATGATGTGT CTAACTGTCG

GTGTGGGGAC AGGCTGAAGA CCCTAGAGCA GAGGGCGCGG AAGCAGCACC

AGAGGTGCCT GGCACATTCA CTGGTGGGGA CTCCAAACTA CATCGCACCC

GAGGTGCTCC TCCGCAAAGG GTACACTCAA CTCTGTGACT GGTGGAGTGT

TGGAGTGATT CTCTTCGAGA TGCTGGTGGG GCAGCCGCCC TTTTTGGCAC

CTACTCCCAC AGAAACCCAG CTGAAGGTGA TCAACTGGGA GAACACGCTC

CACATTCCAG CCCAGGTGAA GCTGAGCCCT GAGGCCAGGG ACCTCATCAC

CAAGCTGTGC TGCTCCGCAG ACCACCGCCT GGGGCGGAAT GGGGCCGATG

ACCTGAAGGC CCACCCCTTC TTCAGCGCCA TTGACTTCTC CAGTGACATC

CGGAAGCATC CAGCCCCCTA CGTTCCCACC ATCAGCCACC CCATGGAG

Name: S51771k

Nucleotide sequence:

TCCCGCTGGACGTGGAGTACGGAGGCCCAGACCGGAGGTGCCCGCCTCCGCCCTACCCGAAGCACCTGCTGC (SEQ ID NO:15)

TGCGCAGCAAGTCGGAGCAGTACGACCTGGACAGCCTGTGCGCAGGCATGGAGCAGAGCCTCCGTGCGGGCC

CCAACGAGCCCGAGGGCGGCGACAAGAGCCGCAAAAGCGCCAAGGGGGACAAAGGCGGAAAGGATAAAAAGC

AGATTCAGACCTCTCCCGTTCCCGTCCGCAAAAACAGCAGAGACGAAGAGAAGAGAGAGTCACGCATCAAGA

GCTACTCGCCATACGCCTTTAAGTTCTTCATGGAGCAGCACGTGGAGAATGTCATCAAAACCTACCAGCAGA

AGGTTAACCGGAGGCTGCAGCTGGAGCAAGAAATGGCCAAAGCTGGACTCTGTGAAGCTGAGCAGGAGCAGA

TGCGGAAGATCCTCTACCAGAAAGAGTCTAATTACAACAGGTTAAAGAGGGCCAAGATGGACAAGTCTATGT

TTGTCAAGATCAAAACCCTGGGGATCGGTGCCTTTGGAGAAGTGTGCCTTGCTTGTAAGGTGGACACTCACG

-continued

```
CCCTGTACGCCATGAAGACCCTAAGGAAAAAGGATGTCCTGAACCGGAATCAGGTGGCCCACGTCAAGGCCG

AGAGGGACATCCTGGCCGAGGCAGACAATGAGTGGGTGGTCAACCTCTACTACTCCTTCCAAGACAAAGACA

GCCTGTACTTTGTGATGGACTACATCCCTGGTGGGGACATGATGAGCCTGCTGATCCGGATGGAGGTCTTCC

CTGAGCACCTGGCCCGGTTCTACATCGCAGAGCTGACTTTGGCCATTGAGAGTGTCCACAAGATGGGCTTCA

TCCACCGAGACATCAAGCCTGATAACATTTTGATAGATCTGGATGGTCACATTAAACTCACAGATTTCGGCC

TCTGCACTGGGTTCAGGTGGACTCACAATTCCAAATATTACCAGAAAGGGAGCCATGTCAGACAGGACAGCA

TGGAGCCCAGCGACCTCTGGGATGATGTGTCTAACTGTCGGTGTGGGGACAGGCTGAAGACCCTAGAGCAGA

GGGCGCGGAAGCAGCACCAGAGGTGCCTGGCACATTCACTGGTGGGGACTCCAAACTACATCGCACCCGAGG

TGCTCCTCCGCAAAGGGTACACTCAACTCTGTGACTGGTGGAGTGTTGGAGTGATTCTCTTCGAGATGCTGG

TGGGGCAGCCGCCCTTTTTGGCACCTACTCCCACAGAAACCCAGCTGAAGGTGATCAACTGGGAGAACACGC

TCCACATTCCAGCCCAGGTGAAGCTGAGCCCTGAGGCCAGGGACCTCATCACCAAGCTGTGCTGCTCCGCAG

ACCACCGCCTGGGGCGGAATGGGGCCGATGACCTGAAGGCCCACCCCTTCTTCAGCGCCATTGACTTCTCCA

GTGACATCCGGAAGCATCCAGCCCCCTACGTTCCCACCATCAGCCACCCCATGGACACCTCGAATTTCGACC

CCGTAGATGAAGAAAGCCCTTGGAACGATGCCAGCGAAGGTAGCACCAAGGCCTGGGACACACTCACCTCGC

CCAATAACAAGCATCCTGAGCACGCATTTTACGAATTCACCTTCCGAAGGTTCTTTGATGACAATGGCTACC

CCTTTCGATGCCCAAAGCCTTCAGGAGCAGAAGCTTCACAGGCTGAGAGCTCAGATTTAGAAAGCTCTGATC

TGGTGGATCAGACTGAAGGCTGCCAGCCTGTGTACGTGTAGATGGGGCCAGGCACCCCCACCACTCGCTGC

CTCCCAGGTCAGGGTCCCGGAGCCGGTGCCCTCACAGGCCAATAGGGAAGCCGAGGGCTGTTTTGTTTTAAA

TTAGTCCGTCGATTACTTCACTTGAAATTCTGCTCTTCACCAAGAAAACCCAAACAGGACACTTTTGAAAAC

AGCGGTGCCGCGAATTC.
```

With the continued increase in the number of known eukaryotic protein kinases, a suitable classification scheme is one based on comparing catalytic-domain sequences. It follows that protein kinases with similar catalytic domains will tend also to have similar enzymatic and regulatory properties. The nucleotide sequences of the invention encode, respectively, the following polypeptides having kinase function:

NAME: HH0900-BF04 Polypeptide

Translation in relevant reading frame (3'–5' Frame 3):

YAMKVLRKAALVQRAKTQEHTRTERSV-LELVRQAPFLVTLHYAFQTDAKLHLILDY VSGG (SEQ ID NO:7);

The above sequence is consistent with the consensus sequence of subdomains II through V of the eukaryotic protein kinase superfamily. This sequence is the sequence of a polypeptide having kinase activity encoded by the nucleotide sequence of SEQ ID NO:1.

NAME: HH2040-BF04 Polypeptide

Translation in relevant reading frame (5'–3' Frame 2):

REVPHQTASDFVRDSAASHQAEPEAYER-RVCFLLLQLCNGLE HLKEHGIIHRDLCLEN-LLLVHCTLQAGPGPA (SEQ ID NO:8);

The above sequence is consistent with the consensus sequence of subdomains V, VIA and VIB of the eukaryotic protein kinase superfamily. This sequence is the sequence of a polypeptide having kinase activity encoded by the nucleotide sequence of SEQ ID NO:2.

Name: JJ503-KS Polypeptide

Translation in relevant reading frame (5'–3' frame 1):

(SEQ ID NO:9)
GQGWSWAGIPSSAAAQRAGPPAGALEALSPGGARAHAERRGEMRATPLAA

PAGSLSRKKRLELDDNLDTERPVQKRARSGPQPRLPPCLLPLSPPTAPDR

ATAVATASRLGPYVLLEPEEGGRAYQALHCPTGTEYTCKVYPVQEALAVL

EPYARLPPHKHVARPTEVLAGTQLLYAFFTRTHGDMHSLVRSRHRIPEPE

AAVLFRQMATALAHCHQHGLVLRDLKLCRFVFADRERKKLVLENLEDSCV

LTGPDDSLWDKHACPAYVGPEILSSRASYSGKAADVWSLGVALFTMLAGH

YPFQDSEPVLLFGKIRRGAYALPAGLSAPARCLVRCLLRREPAERLTATG

ILLHPWLRQD;

The sequence is consistent with kinase domains VIA through XI, though the homology is imperfect. This sequence is the sequence of a polypeptide having kinase activity encoded by the nucleotide sequence of SEQ ID NO:3.

Name: QQ1249-BF04 Polypeptide

Translation in relevant reading frame (5'–3' frame 3)

(SEQ ID NO:10)
QREADMHRLFNHPNILRLVAYCLRERGAKHEAWLLLPFFKRGTLWNEIER

LKDKGNFLTEDQILWLLLGICRGLEAIHAKGYAYRDLKPTNILLGDEGQP

VLMDLGSMNQACIHVEGSRQALTLQDWAAQRCTISYRAPXLFSVQS

The above sequence is consistent with the consensus sequence of subdomains III–VIII of the eukaryotic protein kinase superfamily. This sequence is the sequence of a polypeptide having kinase activity encoded by the nucleotide sequence of SEQ ID NO:4.
Name: QQ3351-BF04 Polypeptide
Translation in relevant frame (5'–3' frame 1)

```
MLTSLNRSWNETTCCGRASFLELCTGQIGRTPLGRREGMENLKHIITLGQVIHKRCEEMKYCKKQCRRLGHR (SEQ ID NO:11)

VLGLIKPLEMLQDQGKRSVPSEKLTTAMNRFKAALEEANGEIEKFSNRSNICRFLTASQDKILFKDVNRKLS

DVWKELSLLLQVEQRMPVSPISQGASWAQEDQQDADEDRRAFQMLRRDNEKIEASLRRLEINMKEIKETLRQ

YLPPKCMQEIPQEQIKEIKKEQLSGSPWILLREMEVSTLYKGEYHRAPVAIKVFKKLQAGSIAIVRQTFNKE

IKTMKKFESPNILRIFGICIDETVTPPQFSIVMEYCELGTLRELLDREKDLTLGKRMVLVLGAARGLYRLHH

SEAPELHGKIRSSNFLVTQGYQVKLAGFELRKTQTSMSLGTTREKTDRVKSTAYLSPQELEDVFYQYDVKSE

IYSFGIVLWEIATGDIPFQGCNSEKIRKLVAVKRQQEPLGEDCPSELREIIDECRAAGRLVPRSVAAARAVDV
```

The above sequence is believed to be full-length. However, the initial methionine was not present in the clone sequenced but subsequently was added by PCR. Therefore, the natural sequence may comprise Leu-2 through the Val-505. This sequence is the sequence of a polypeptide having kinase activity encoded by the nucleotide sequence of SEQ ID NO:5.
Name: SS1771
Translation in relevant frame (3'–5' frame 3)

```
                                                        (SEQ ID NO:12)
FPLDVEYGGPDRRCPPPPYPKHLLLRSKSEQYDLDSLCAGMEQSLRAGPN

EPEGGDKSRKSAKGDKGGKDKKQIQTSPVPVRKNSRDEEKRESRIKSYSP

YAFKFFMEQHVENVIKTYQQKVNRRLQLEQEMAKAGLCEAEQEQMRKILY

QKESNYNRLKRAKMDKSMFVKIKTLGIGAFGEVCLACKVDTHALYAMKTL

RKKDVLNRNQVAHVKAERDILAEADNEWVVKLYYSFQDKDSLYFVMDYIP

GGDMMSLLIRMEVFPEHLARFYIAELTLAIESVHKMGFIHRDIKPDNILI

DLDGHIKLTDFGLCTGFRWTHNSKYYQKGSHVRQDSMEPSDLWDDVSNCR

CGDRLKTLEQRARKQHQRCLAHSLVGTPNYIAPEVLLRKGYTQLCDWWSV
```

-continued
```
GVILFEMLVGQPPFLAPTPTETQLKVINWENTLHIPAQVKLSPEARDLIT

KLCCSADHRLGRNGADDLKAHPFFSAIDFSSDIRKHPAPYVPTISHPME
```

This sequence is the sequence of a polypeptide having kinase activity encoded by the nucleotide sequence of SEQ ID NO:6. The sequence may also comprise Pro-2 through Glu499.
Name: SS1771A
Translation in relevant frame (5'–3' frame 3)

```
PLDVEYGGPDRRCPPPPYPKHLLLRSKSEQYDLDSLCAGMEQSLRAGPNEPEGGDKSRKSAKGDKGGKDKKQ (SEQ ID NO:16)

IQTSPVPVRKNSRDEEKRESRIKSYSPYAFKFFMEQHVENVIKTYQQKVNRRLQLEQEMAKAGLCEAEQEQM

RKILYQKESNYNRLKRAKMDKSMFVKIKTLGIGAFGEVCLACKVDTHALYAMKTLRKKDVLNRNQVAHVKAE

RDILAEADNEWVVKLYYSFQDKDSLYFVMDYIPGGDMMSLLIRMEVFPEHLARFYIAELTLAIESVHKMGFI

HRDIKPDNILIDLDGHIKLTDFGLCTGFRWTHNSKYYQKGSHVRQDSMEPSDLWDDVSNCRCGDRLKTLEQR

ARKQHQRCLAHSLVGTPNYIAPEVLLRKGYTQLCDWWSVGVILFEMLVGQPPFLAPTPTETQLKVINWENTL

HIPAQVKLSPEARDLITKLCCSADHRLGRNGADDLKAHPFFSAIDFSSDIRKHPAPYVPTISHPMDTSNFDP

VDEESPWNDASEGSTKAWDTLTSPNNKHPEHAFYEFTFRRFFDDNGYPFRCPKPSGAEASQAESSDLESSDL

VDQTEGCQPVYV
```

This sequence is the sequence of a polypeptide having kinase activity encoded by the nucleotide sequence of SEQ ID NO:1.

The invention also includes truncated forms of the nucleic acids and polypeptides of the invention. In a preferred embodiment, the invention includes a truncated form of QQ3351-BF04, as follows:

Nucleotide sequence:

```
CTTGCAGGATTTGAGTTGAGGAAAACACAGACTTCCATGAGTTTGGGAACTACGAGAGAAAAGACAGACAGA (SEQ ID NO:13)

GTCAAATCTACAGCATATCTCTCACCTCAGGAACTGGAAGATGTATTTTATCAATATGATGTAAAGTCTGAA

ATATACAGCTTTGGAATCGTCCTCTGGGAAATCGCCACTGGAGATATCCCGTTTCAAGGCTGTAATTCTGAG

AAGATCCGCAAGCTGGTGGCTGTGAAGCGGCAGCAGGAGCCACTGGGTGAAGACTGCCCTTCAGAGCTGCGG

GAGATCATTGATGAGTGCCGGGCCCATGATCCCTCTGTGCGGCCCTCTGTGGATGAAATCTTAAAGAAACTC

TCCACCTTTTCTAAG
```

Translation in relevant frame (5'3' frame 1):

(SEQ ID NO:14)
LAGFELRKTQTSMSLGTTREKTDRVKSTAYLSPQELEDVFYQYDVKSEIYS

FGIVLWEIATGDIPFQGCNSEKIRKLVAVKRQQEPLGEDCPSELREIIDEC

RAHDPSVRPSVDEILKKLSTFSK

This sequence is the sequence of a polypeptide having kinase activity encoded by the nucleotide sequence of SEQ ID NO:13.

The polypeptides of the invention are useful for characterizing cell and tissue expression, understanding their roles in development or hormonal response, and identifying regulatory molecules and physiologically relevant protein substrates.

As used herein, the term "polypeptides of the invention" refers to a genus of polypeptides that further encompasses proteins having the amino acid sequence of SEQ ID NO:7, 8, 9, 10, 11, 12, 14, or 16 as well as those proteins having a high degree of similarity (at least 90% homology) with such amino acid sequences and which proteins are biologically active. In addition, polypeptides of the invention refers to the gene products of the nucleotides of SEQ ID NO:1, 2, 3, 4, 5, 6, 13 or 15.

The isolated and purified polypeptides of the invention have molecular weights of approximately 6883 (HH0900-BF04); 8168 (HH2040-BF04); 39,284 (JJ503-KS); 16,718 (QQ1249-BF04); 58,001 (QQ3351-BF04); 57,381 (SS1771), and 67,331 (SS1771A) Daltons in the absence of glycosylation. It is understood that the molecular weight of these polypeptides can be varied by fusing additional peptide sequences to both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein.

It is understood that fusions of additional peptide sequences at the amino and carboxyl terminal ends of polypeptides of the invention will alter some, but usually not all, of the fragmented peptides of the polypeptides generated by enzymatic or chemical treatment.

It is understood that mutations can be introduced into polypeptides of the invention using routine and known techniques of molecular biology. It is further understood that a mutation can be designed so as to eliminate a site of proteolytic cleavage by a specific enzyme or a site of cleavage by a specific chemically induced fragmentation procedure. It is also understood that the elimination of the site will alter the peptide fingerprint of polypeptides of the invention upon fragmentation with the specific enzyme or chemical procedure.

The term "isolated and purified" as used herein, means that the polypeptides or fragments of the invention are essentially free of association with other proteins or polypeptides, for example, as a purification product of recombinant host cell culture or as a purified product from a non-recombinant source. The term "substantially purified" as used herein, refers to a mixture that contains polypeptides or fragments of the invention and is essentially free of association with other proteins or polypeptides, but for the presence of known proteins that can be removed using a specific antibody, and which substantially purified polypeptides or fragments thereof can be used as molecular weight markers. The term "purified" refers to either the "isolated and purified" form of polypeptides of the invention or the "substantially purified" form of polypeptides of the invention, as both are described herein.

A polypeptide "variant" as referred to herein means a polypeptide substantially homologous to native polypeptides of the invention, but which has an amino acid sequence different from that of native polypeptides (human, murine or other mammalian species) of the invention because of one or more deletions, insertions or substitutions. The variant amino acid sequence preferably is at least 80% identical to a native polypeptide amino acid sequence, most preferably at least 90% identical. The percent identity can be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring variants are also encompassed by the invention. Examples of such variants are proteins that result from alternate mRNA splicing events, proteolytic cleavage of the polypeptides, or transcription/translation from different alleles. Variations attributable to proteolysis include, for example, differences in the N- or C-termini upon expression in different types of host cells, due to proteolytic removal of one or more terminal amino acids from the polypeptides (generally from 1–5 terminal amino acids) of the invention.

The polypeptides of the invention can also exist as oligomers, such as covalently linked or non-covalently linked dimers or trimers. Oligomers can be linked by disulfide bonds formed between cysteine residues on different polypeptides.

In one embodiment of the invention, a polypeptide dimer is created by fusing polypeptides of the invention to the Fc region of an antibody (e.g., IgG1) in a manner that does not interfere with the biological activity of these polypeptides. The Fc region preferably is fused to the C-terminus of a soluble polypeptide of the invention, to form an Fc fusion or an Fc polypeptide. The terms "Fc fusion protein" or "Fc polypeptides" as used herein includes native and mutein forms, as well as truncated Fc polypeptides containing the hinge region that promotes dimerization. Exemplary methods of making Fc polypeptides set forth above are disclosed in U.S. Pat. Nos. 5,426,048 and 5,783,672 both of which are incorporated herein by reference.

In a preferred embodiment, extracellular domains from transmembrane bound kinases are fused to Fc portions of antibodies to produce soluble Fc polypeptides. These constructs can function as binding sites for the ligand that naturally binds the kinase receptor and thereby inhibit binding of the ligand to the natural receptor.

General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference. A gene fusion encoding the polypeptide:Fc fusion protein of the invention is inserted into an appropriate expression vector. Polypeptide:Fc fusion proteins are allowed to assemble much like antibody molecules, whereupon interchain disulfide bonds form between Fc polypeptides, yielding divalent polypeptides of the invention. If fusion proteins are made with both heavy and light chains of an antibody, it is possible to form a polypeptide oligomer with as many as four polypeptides extracellular regions. Alternatively, one can link two soluble polypeptide domains with a peptide linker.

In one embodiment of this invention, the polypeptides of the invention are produced by recombinant expression. In one preferred embodiment, the expression of recombinant polypeptides having kinase functions can be accomplished utilizing fusion of sequences encoding polypeptides having kinase functions to sequences encoding another polypeptide to aid in the purification of polypeptides of the invention. An example of such a fusion is a fusion of sequences encoding a polypeptide having kinase functions to sequences encoding the product of the malE gene of the pMAL-c2 vector of New England Biolabs, Inc. Such a fusion allows for affinity purification of the fusion protein, as well as separation of the maltose binding protein portion of the fusion protein from the polypeptide of the invention after purification.

The insertion of DNA encoding the polypeptide having kinase functions into the pMAL-c2 vector can be accomplished in a variety of ways using known molecular biology techniques. The preferred construction of the insertion contains a termination codon adjoining the carboxyl terminal codon of the polypeptide of the invention. In addition, the preferred construction of the insertion results in the fusion of the amino terminus of the polypeptide of the invention directly to the carboxyl terminus of the Factor Xa cleavage site in the pMAL-c2 vector. A DNA fragment can be generated by PCR using DNA of the invention as the template DNA and two oligonucleotide primers. Use of the oligonucleotide primers generates a blunt-ended fragment of DNA that can be isolated by conventional means. This PCR product can be ligated together with pMAL-p2 (digested with the restriction endonuclease Xmn I) using conventional means. Positive clones can be identified by conventional means. Induction of expression and purification of the fusion protein can be performed as per the manufacturer's instructions. This construction facilitates a precise separation of the polypeptide of the invention from the fused maltose binding protein utilizing a simple protease treatment as per the manufacturer's instructions. In this manner, purified polypeptide having kinase functions can be obtained. Furthermore, such a constructed vector can be easily modified using known molecular biology techniques to generate additional fusion proteins. It is understood, of course, that many different vectors and techniques can be used for the expression and purification of polypeptides of the invention and that this embodiment in no way limits the scope of the invention.

Polypeptides of the invention can be subjected to fragmentation into peptides by chemical and enzymatic means. Chemical fragmentation includes the use of cyanogen bromide to cleave under neutral or acidic conditions such that specific cleavage occurs at methionine residues (E. Gross, *Methods in Enz.* 11:238–255, 1967). This can further include additional steps, such as a carboxymethylation step to convert cysteine residues to an unreactive species. Enzymatic fragmentation includes the use of a protease such as Asparaginylendopeptidase, Arginylendo-peptidase, Achromobacter protease I, Trypsin, *Staphlococcus aureus* V8 protease, Endoproteinase Asp-N, or Endoproteinase Lys-C under conventional conditions to result in cleavage at specific amino acid residues. Asparaginylendo-peptidase can cleave specifically on the carboxyl side of the asparagine residues present within the polypeptides of the invention. Arginylendo-peptidase can cleave specifically on the carboxyl side of the arginine residues present within these polypeptides. Achromobacter protease I can cleave specifically on the carboxyl side of the lysine residues present within the polypeptides (Sakiyama and Nakat, U.S. Pat. No. 5,248,599; T. Masaki et al., *Biochim. Biophys. Acta* 660:44–50, 1981; T. Masaki et al., *Biochim. Biophys. Acta* 660:51–55, 1981). Trypsin can cleave specifically on the carboxyl side of the arginine and lysine residues present within polypeptides of the invention. *Staphlococcus aureus* V8 protease can cleave specifically on the carboxyl side of the aspartic and glutamic acid residues present within polypeptides (D. W. Cleveland, *J. Biol. Chem.* 3:1102–1106, 1977). Endoproteinase Asp-N can cleave specifically on the amino side of the asparagine residues present within polypeptides. Endoproteinase Lys-C can cleave specifically on the carboxyl side of the lysine residues present within polypeptides of the invention. Other enzymatic and chemical treatments can likewise be used to specifically fragment these polypeptides into a unique set of specific peptide molecular weight markers.

The resultant fragmented peptides can be analyzed by methods including sedimentation, electrophoresis, chromatography, and mass spectrometry. The fragmented peptides derived from the polypeptides of the invention can serve as molecular weight markers using such analysis techniques to assist in the determination of the molecular weight of a sample protein. Such a molecular weight determination assists in the identification of the sample protein. Fragmented peptide molecular weight markers of the invention are preferably at least 10 amino acids in size. More preferably, these fragmented peptide molecular weight markers are between 10 and 100 amino acids in size. Even more preferable are fragmented peptide molecular weight markers between 10 and 50 amino acids in size and especially between 10 and 35 amino acids in size. Most preferable are fragmented peptide molecular weight markers between 10 and 20 amino acids in size.

Furthermore, analysis of the progressive fragmentation of the polypeptides of the invention into specific peptides (D. W. Cleveland et al., *J. Biol. Chem.* 252:1102–1106, 1977), such as by altering the time or temperature of the fragmentation reaction, can be used as a control for the extent of cleavage of a sample protein. For example, cleavage of the same amount of polypeptide and sample protein under identical conditions can allow for a direct comparison of the extent of fragmentation. Conditions that result in the complete fragmentation of the polypeptide can also result in complete fragmentation of the sample protein.

In addition, the polypeptides and fragmented peptides of the invention possess unique charge characteristics and, therefore, can serve as specific markers to assist in the determination of the isoelectric point of a sample protein or fragmented peptide using techniques such as isoelectric focusing. The technique of isoelectric focusing can be further combined with other techniques such as gel electrophoresis to simultaneously separate a protein on the basis of molecular weight and charge. An example of such a combination is that of two-dimensional electrophoresis (T. D. Brock and M. T. Madigan, *Biology of Microorganisms* 76–77 (Prentice Hall, 6d ed. 1991)). These polypeptides and fragmented peptides thereof can be used in such analyses as markers to assist in the determination of both the isoelectric point and molecular weight of a sample protein or fragmented peptide.

Kits to aid in the determination of apparent molecular weight and isoelectric point of a sample protein can be assembled from the polypeptides and peptide fragments of the invention. Kits also serve to assess the degree of fragmentation of a sample protein. The constituents of such kits can be varied, but typically contain the polypeptide and fragmented peptide molecular weight markers. Also, such kits can contain the polypeptides wherein a site necessary for fragmentation has been removed. Furthermore, the kits can contain reagents for the specific cleavage of the polypeptide and the sample protein by chemical or enzymatic cleavage. Kits can further contain antibodies directed against polypeptides or fragments thereof of the invention.

The isolated and purified polypeptides of the invention have molecular weights of approximately 6883 (HH0900-BF04); 8168 (HH2040-BF04); 39,284 (JJ503-KS); 16,718 (QQ1249-BF04); 58,001 (QQ3351-BF04); 57,381 (SS1771), and 67,331 (SS1771A) Daltons in the absence of glycosylation. The polypeptide of the invention, together with a sample protein, can be resolved by denaturing polyacrylamide gel electrophoresis by conventional means (U. K. Laemmli, *Nature* 227:680–685, 1970) in two separate lanes of a gel containing sodium dodecyl sulfate and a concentration of acrylamide between 6–20%. Proteins on the gel can be visualized using a conventional staining procedure. The polypeptide molecular weight markers of the invention can be used as molecular weight marker in the estimation of the apparent molecular weight of the sample protein. The unique amino acid sequence of SEQ ID NO:7, 8, 9, 10, 11, 12, and 16 correspond to molecular weight of approximately 6883; 8168; 39,284; 16,718; 58,001; 57,381; or 67,331 Daltons, respectively. Therefore, the polypeptide molecular weight markers serve particularly well as a molecular weight marker for the estimation of the apparent molecular weight of sample proteins that have apparent molecular weights close to 6883; 8168; 39,284; 16,718; 58,001; 57,381; or 67,331 Daltons. The use of these polypeptide molecular weight markers allows increased accuracy in the determination of apparent molecular weight of proteins that have apparent molecular weights close to 6883; 8168; 39,284; 16,718; 28,982; or 57,381 Daltons. It is understood of course that many different techniques can be used for the determination of the molecular weight of a sample protein using polypeptides of the invention, and that this embodiment in no way limits the scope of the invention.

Another preferred embodiment of the invention is the use of polypeptides and fragmented peptides of the invention as molecular weight markers to estimate the apparent molecular weight of a sample protein by gel electrophoresis. These fragmented peptides can be generated methods well known in the art such as chemical fragmentation. Isolated and purified polypeptides of the invention can be treated with cyanogen bromide under conventional conditions that result in fragmentation of the polypeptide molecular weight marker by specific hydrolysis on the carboxyl side of the methionine residues within the polypeptides of the invention (E. Gross, *Methods in Enz.* 11:238–255, 1967). Due to the unique amino acid sequence of the polypeptides of the invention, the fragmentation of polypeptide molecular weight markers with cyanogen bromide generates a unique set of fragmented peptide molecular weight markers. The distribution of methionine residues determines the number of amino acids in each peptide and the unique amino acid composition of each peptide determines its molecular weight. Polypeptide molecular weight markers of the invention can be analyzed by methods including sedimentation, gel electrophoresis, chromatography, and mass spectrometry.

The fragmented peptide molecular weight markers of the invention, together with a sample protein, can be resolved by denaturing polyacrylamide gel electrophoresis by conventional means in two separate lanes of a gel containing sodium dodecyl sulfate and a concentration of acrylamide between 10–20%. Proteins on the gel can be visualized using a conventional staining procedure. The fragmented peptide molecular weight markers of the invention can be used as molecular weight markers in the estimation of the apparent molecular weight of the sample protein. The unique amino acid sequence of each marker specifies a molecular weight. Therefore, the fragmented peptide molecular weight markers serve particularly well as molecular weight markers for the estimation of the apparent molecular weight of sample proteins that have similar apparent molecular weights. Consequently, the use of these fragmented peptide molecular weight markers allows increased accuracy in the determination of apparent molecular weight of proteins.

Polypeptides on the membrane can be visualized using two different methods that allow a discrimination between the sample protein and the molecular weight markers. Polypeptide or fragmented peptide molecular weight markers of the invention can be visualized using antibodies generated against these markers and conventional immunoblotting techniques. This detection is performed under conventional conditions that do not result in the detection of the sample protein. It is understood that it may not be possible to generate antibodies against all polypeptide fragments of the invention, since small peptides may not contain immunogenic epitopes. It is further understood that not all antibodies will work in this assay; however, those antibodies which are able to bind polypeptides and fragments of the invention can be readily determined using conventional techniques.

The sample protein is visualized using a conventional staining procedure. The molar excess of sample protein to polypeptide or fragmented peptide molecular weight markers of the invention is such that the conventional staining procedure predominantly detects the sample protein. The level of these polypeptide or fragmented peptide molecular weight markers is such as to allow little or no detection of these markers by the conventional staining method. The preferred molar excess of sample protein to polypeptide molecular weight markers of the invention is between 2 and 100,000 fold. More preferably, the preferred molar excess of sample protein to these polypeptide molecular weight markers is between 10 and 10,000 fold and especially between 100 and 1,000 fold.

The polypeptide or fragmented peptide molecular weight markers of the invention can be used as molecular weight and isoelectric point markers in the estimation of the apparent molecular weight and isoelectric point of the sample protein. These polypeptide or fragmented peptide molecular weight markers serve particularly well as molecular weight and isoelectric point markers for the estimation of apparent molecular weights and isoelectric points of sample proteins that have apparent molecular weights and isoelectric points close to that of the polypeptide or fragmented peptide molecular weight markers of the invention. The ability to simultaneously resolve these polypeptide or fragmented peptide molecular weight markers and the sample protein under identical conditions allows for increased accuracy in the determination of the apparent molecular weight and isoelectric point of the sample protein. This is of particular interest in techniques, such as two dimensional electrophoresis, where the nature of the procedure dictates that any markers should be resolved simultaneously with the sample protein.

In another embodiment, polypeptide or fragmented peptide molecular weight markers of the invention can be used as molecular weight and isoelectric point markers in the estimation of the apparent molecular weight and isoelectric point of fragmented peptides derived by treatment of a sample protein with a cleavage agent. It is understood of course that many techniques can be used for the determination of molecular weight and isoelectric point of a sample protein and fragmented peptides thereof using these polypeptide molecular weight markers and peptide fragments thereof and that this embodiment in no way limits the scope of the invention.

Polypeptide molecular weight markers encompassed by invention can have variable molecular weights, depending upon the host cell in which they are expressed. Glycosylation of polypeptide molecular weight markers and peptide fragments of the invention in various cell types can result in variations of the molecular weight of these markers, depending upon the extent of modification. The size of these polypeptide molecular weight markers can be most heterogeneous with fragments of polypeptide derived from the extracellular portion of the polypeptide. Consistent molecular weight markers can be obtained by using polypeptides derived entirely from the transmembrane and cytoplasmic regions, pretreating with N-glycanase to remove glycosylation, or expressing the polypeptides in bacterial hosts.

As stated above, the invention provides isolated and purified polypeptides, both recombinant and non-recombinant. Variants and derivatives of native polypeptides can be obtained by mutations of nucleotide sequences coding for native polypeptides. Alterations of the native amino acid sequence can be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); Kunkel (*Proc. Natl. Acad. Sci USA* 82:488, 1985); Kunkel et al. (*Methods in Enzymol.* 154:367, 1987); and U.S. Pat. Nos. 4,518,584 and 4,737,462, all of which are incorporated by reference.

Polypeptides of the invention can be modified to create polypeptide derivatives by forming covalent or aggregative conjugates with other chemical moieties, such as glycosyl groups, polyethylene glycol (PEG) groups, lipids, phosphate, acetyl groups and the like. Covalent derivatives of polypeptides of the invention can be prepared by linking the chemical moieties to functional groups on polypeptide amino acid side chains or at the N-terminus or C-terminus of a polypeptide of the invention or the extracellular domain thereof. Other derivatives of polypeptides within the scope of this invention include covalent or aggregative conjugates of these polypeptides or peptide fragments with other proteins or polypeptides, such as by synthesis in recombinant culture as N-terminal or C-terminal fusions. For example, the conjugate can comprise a signal or leader polypeptide sequence (e.g. the α-factor leader of Saccharomyces) at the N-terminus of a polypeptide of the invention. The signal or leader peptide co-translationally or post-translationally directs transfer of the conjugate from its site of synthesis to a site inside or outside of the cell membrane or cell wall.

Polypeptide conjugates can comprise peptides added to facilitate purification and identification of polypeptides of the invention. Such peptides include, for example, poly-His or the antigenic identification peptides described in U.S. Pat. No. 5,011,912 and in Hopp et al., *Bio/Technology* 6:1204, 1988.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, equivalent DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding, or substituting residues to alter Arg—Arg, Arg-Lys, and Lys-Arg pairs to eliminate the occurrence of these adjacent basic residues. Lys—Lys pairings are considerably less susceptible to KEX2 cleavage, and conversion of Arg-Lys or Lys-Arg to Lys—Lys represents a conservative and preferred approach to inactivating KEX2 sites.

The invention further encompasses isolated fragments and oligonucleotides derived from the nucleotide sequence of SEQ ID NO:1, 2, 3, 4, 5, 6, 13 or 15. Nucleic acid sequences within the scope of the invention include isolated DNA and RNA sequences that hybridize to the native nucleotide sequences disclosed herein under conditions of moderate or severe stringency, and which encode polypeptides or fragments thereof of the invention. These isolated DNA and RNA sequences also include full length DNA or RNA molecules encoding for polypeptides with kinase activity. As used herein, conditions of moderate stringency, as known to those having ordinary skill in the art, and as defined by Sambrook et al. *Molecular Cloning: A Laboratory Manual*, 2 ed. Vol. 1, pp. 1.101–104, Cold Spring Harbor Laboratory Press, (1989), include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of about 60° C., 0.5×SSC, 0.1% SDS. Conditions of high stringency are defined as hybridization conditions as above, and with washing at 68° C., 0.2×SSC, 0.1% SDS. The skilled artisan will recognize that the temperature and wash solution salt concentration can be adjusted as necessary according to factors such as the length of the probe.

Due to the known degeneracy of the genetic code, wherein more than one codon can encode the same amino acid, a DNA sequence can vary from that shown in SEQ ID NO:1, 2, 3, 4, 5, 6, 13 or 15, and still encode a polypeptide having the amino acid sequence of SEQ ID NO:7, 8, 9, 10, 11, 12, 14 or 16. Such variant DNA sequences can result from silent mutations (e.g., occurring during PCR amplification), or can be the product of deliberate mutagenesis of a native sequence.

The invention thus provides equivalent isolated DNA sequences encoding polypeptides of the invention, selected from: (a) DNA derived from the coding region of a native mammalian gene; (b) cDNA comprising the nucleotide sequence of SEQ ID NO: 1, 2, 3,4, 5, 6, 13 or 15; (c) DNA encoding the polypeptides of SEQ ID NO:7, 8,9, 10, 11, 12, 14 or 16; (d) DNA capable of hybridization to a DNA of (a) under conditions of moderate stringency and which encodes polypeptides of the invention; and (e) DNA which is degenerate as a result of the genetic code to a DNA defined in (a), (b), (c), or (d) and which encodes polypeptides of the invention. Of course, polypeptides encoded by such DNA equivalent sequences are encompassed by the invention.

DNA that is equivalent to the DNA sequence of SEQ ID NO:1, 2, 3, 4, 5, 6, 13 or 15 will hybridize under moderately stringent conditions to the double-stranded native DNA sequence that encode polypeptides comprising amino acid sequences of SEQ ID NO:7, 8, 9, 10, 11, 12, 14 or 16. Examples of polypeptides encoded by such DNA, include, but are not limited to, polypeptide fragments and polypeptides comprising inactivated N-glycosylation site(s), inactivated protease processing site(s), or conservative amino acid substitution(s), as described above. Polypeptides encoded by DNA derived from other mammalian species, wherein the DNA will hybridize to the complement of the DNA of SEQ ID NO:1, 2, 3, 4, 5, 6, 13 or 15 are also encompassed.

Recombinant expression vectors containing a nucleic acid sequence encoding polypeptides of the invention can be prepared using well known methods. The expression vectors include a DNA sequence of the invention operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the DNA sequence of the invention. Thus, a promoter nucleotide sequence is operably linked to a DNA sequence if the promoter nucleotide sequence controls the transcription of the DNA sequence of the invention. The ability to replicate in the desired host cells, usually conferred by an origin of replication, and a selection gene by which transformants are identified can additionally be incorporated into the expression vector.

In addition, sequences encoding appropriate signal peptides that are not naturally associated with polypeptides of the invention can be incorporated into expression vectors. For example, a DNA sequence for a signal peptide (secretory leader) can be fused in-frame to the nucleotide sequence of the invention so that the polypeptide is initially translated as a fusion protein comprising the signal peptide. A signal peptide that is functional in the intended host cells enhances extracellular secretion of the polypeptide. The signal peptide can be cleaved from the polypeptide upon secretion of polypeptide from the cell.

Suitable host cells for expression of polypeptides of the invention include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce polypeptides of the invention using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera Pseudomonas, Streptomyces, and Staphylococcus. In a prokaryotic host cell, such as *E. coli*, a polypeptide of the invention can include an N-terminal methionine residue to facilitate expression of the recombinant polypeptide in the prokaryotic host cell. The N-terminal Met can be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence of the invention are inserted into the pBR322 vector. Other commercially available vectors include, for example, pKK223-3 (Pharmacia Fine Chemicals, Uppsala, Sweden) and PGEM1 (Promega Biotec, Madison, Wis., USA). Other commercially available vectors include those that are specifically designed for the expression of proteins; these would include pMAL-p2 and pMAL-c2 vectors that are used for the expression of proteins fused to maltose binding protein (New England Biolabs, Beverly, Mass., USA).

Promoter sequences commonly used for recombinant prokaryotic host cell expression vectors include P-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776), and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection, which incorporate derivatives of the $\lambda P_L$ promoter, include plasmid pHUB2 (resident in *E. coli* strain JMB9 (ATCC 37092)) and pPLc28 (resident in *E. coli* RR1 (ATCC 53082)).

DNA of the invention can be cloned in-frame into the multiple cloning site of an ordinary bacterial expression vector. Ideally the vector contains an inducible promoter upstream of the cloning site, such that addition of an inducer leads to high-level production of the recombinant protein at a time of the investigator's choosing. For some proteins, expression levels can be boosted by incorporation of codons encoding a fusion partner (such as hexahistidine) between the promoter and the gene of interest. The resulting "expression plasmid" can be propagated in a variety of prokaryotic hosts such as *E. coli*.

For expression of the recombinant protein, the bacterial cells are propagated in growth medium until reaching a pre-determined optical density. Expression of the recombinant protein is then induced, e.g. by addition of IPTG (isopropyl-b-D-thiogalactopyranoside), which activates expression of proteins from plasmids containing a lac operator/promoter. After induction (typically for 1–4 hours), the cells are harvested by pelleting in a centrifuge, e.g. at 5,000×G for 20 minutes at 4° C.

For recovery of the expressed protein, the pelleted cells may be resuspended in ten volumes of 50 mM Tris-HCl (pH 8)/1 M NaCl and then passed two or three times through a French press. Most highly-expressed recombinant proteins form insoluble aggregates known as inclusion bodies. Inclusion bodies can be purified away from the soluble proteins by pelleting in a centrifuge at 5,000×G for 20 minutes, 4° C. The inclusion body pellet is washed with 50 mM Tris-HCl (pH 8)/1% Triton X-100 and then dissolved in 50 mM Tris-HCl (pH 8)/8 M urea/0.1 M DTT. Any material that cannot be dissolved is removed by centrifugation (10,000×G for 20 minutes, 20° C.). The protein of interest will, in most cases, be the most abundant protein in the resulting clarified supernatant. This protein may be "refolded" into the active conformation by dialysis against 50 mM Tris-HCl (pH 8)/5 mM $CaCl_2$/5 mM $Zn(OAc)_2$/1 mM GSSG/0.1 mM GSH. After refolding, purification can be carried out by a variety of chromatographic methods such as ion exchange or gel filtration. In some protocols, initial purification may be carried out before refolding. As an example, hexahistidine-tagged fusion proteins may be partially purified on immobilized nickel.

While the preceding purification and refolding procedure assumes that the protein is best recovered from inclusion bodies, those skilled in the art of protein purification will appreciate that many recombinant proteins are best purified out of the soluble fraction of cell lysates. In these cases, refolding is often not required, and purification by standard chromatographic methods can be carried out directly.

Polypeptides of the invention alternatively can be expressed in yeast host cells, preferably from the Saccharomyces genus (e.g., *S. cerevisiae*). Other genera of yeast, such as Pichia, *K. lactis*, or Kluyveromyces, can also be employed. Yeast vectors will often contain an origin of replication sequence from a $2\mu$ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980), or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene*, 107:285–195 (1991); and van den Berg et. al., *Bio/Technology*, 8:135–139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* can be constructed by inserting DNA sequences from pBR322 for selection and replication in *E. coli* (Amp gene and origin of replication) into the above-described yeast vectors.

The yeast α-factor leader sequence can be employed to direct secretion of a polypeptide of the invention. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence can be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine, and 20 μg/ml uracil.

Yeast host cells transformed by vectors containing ADH2 promoter sequence can be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant polypeptides of the invention. Baculovirus systems for production of heterologous proteins in insect cells are reviewed by Luckow and Summers, *Bio/Technology* 6:47 (1988). Established cell lines of mammalian origin also can be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line (ATCC CRL 10478) derived from the African green monkey kidney cell line CVI (ATCC CCL 70) as described by McMahan et al. (*EMBO J*. 10: 2821, 1991).

Established methods for introducing DNA into mammalian cells have been described (Kaufman, R. J., *Large Scale Mammalian Cell Culture*, 1990, pp. 15–69). Additional protocols using commercially available reagents, such as Lipofectamine (Gibco/BRL) or Lipofectamine-Plus, can be used to transfect cells (Felgner et al., *Proc. Natl. Acad. Sci. USA* 84:7413–7417, 1987). In addition, electroporation can be used to transfect mammalian cells using conventional procedures, such as those in Sambrook et al. *Molecular Cloning: A Laboratory Manual*, 2 ed. Vol. 1–3, Cold Spring Harbor Laboratory Press, 1989). Selection of stable transformants can be performed using methods known in the art, such as, for example, resistance to cytotoxic drugs. Kaufman et al., *Meth. in Enzymology* 185:487–511, 1990, describes several selection schemes, such as dihydrofolate reductase (DHFR) resistance. A suitable host strain for DHFR selection can be CHO strain DX-B 11, which is deficient in DHFR (Urlaub and Chasin, *Proc. Natl. Acadi Sci. USA* 77:42164220, 1980). A plasmid expressing the DHFR cDNA can be introduced into strain DX-B 11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529–534) and the tripartite leader (TPL) and VA gene RNAs from Adenovirus 2 (Gingeras et al., *J. Biol. Chem*. 257:13475–13491, 1982). The internal ribosome entry site (IRES) sequences of viral origin allows dicistronic mRNAs to be translated efficiently (Oh and Sarnow, *Current Opinion in Genetics and Development* 3:295–300, 1993; Ramesh et al., *Nucleic Acids Research* 24:2697–2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150–161, 1997, and p2A5I described by Morris et al., *Animal Cell Technology*, 1997, pp. 529–534.

A useful high expression vector, pCAVNOT, has been described by Mosley et al., *Cell* 59:335–348, 1989. Other expression vectors for use in mammalian host cells can be constructed as disclosed by Okayama and Berg (*Mol. Cell. Biol*. 3:280, 1983). A useful system for stable high level expression of mammalian cDNAs in C127 murine mammary epithelial cells can be constructed substantially as described by Cosman et al. (*Mol. Immunol*. 23:935, 1986). A useful high expression vector, PMLSV N1/N4, described by Cosman et al., *Nature* 312:768, 1984, has been deposited as ATCC 39890. Additional useful mammalian expression vectors are described in EP-A0367566, and in U.S. patent application Ser. No. 07/701,415, filed May 16, 1991, incorporated by reference herein. The vectors can be derived from retroviruses. In place of the native signal sequence, a heterologous signal sequence can be added, such as the signal sequence for IL-7 described in U.S. Pat. No. 4,965,195; the signal sequence for IL-2 receptor described in Cosman et al., *Nature* 312:768 (1984); the IL4 signal peptide described in EP 367,566; the type I IL-1 receptor signal peptide described in U.S. Pat. No. 4,968,607; and the type II IL-1 receptor signal peptide described in EP 460,846. Another useful expression vector, pFLAG, can be used. FLAG technology is centered on the fusion of a low molecular weight (1 kD), hydrophilic, FLAG marker peptide to the N-Terminus of a recombinants protein expressed by the pFLAG-1™ Expression Vector (1) (obtained from IBI Kodak).

An isolated and purified polypeptide according to the invention can be produced by recombinant expression systems as described above or purified from naturally occurring cells. Polypeptides can be substantially purified, as indicated by a single protein band upon analysis by SDS-polyacrylamide gel electrophoresis (SDS-PAGE).

One process for producing polypeptides of the invention comprises culturing a host cell transformed with an expression vector comprising a DNA sequence that encodes a polypeptide of the invention under conditions sufficient to promote expression of the polypeptide. The polypeptide is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium. For example, when expression systems that secrete the recombinant protein are employed, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify the polypeptides. Some or all of the foregoing purification steps, in various combinations, are well known and can be employed to provide an isolated and purified recombinant protein.

It is possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized.

In this aspect of the invention, polypeptide-binding proteins, such as the anti-polypeptide antibodies of the invention, can be bound to a solid phase such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cel. Biochem.*, 10D:239 (1986). Wash of unbound material and the release of the bound cells is performed using conventional methods.

In the methods described above, suitable polypeptide-binding proteins are anti-polypeptide antibodies, and other proteins that are capable of high-affinity binding of polypeptides of the invention. A preferred polypeptide-binding protein is an polypeptide monoclonal antibody.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express polypeptides of the invention as a secreted polypeptide in order to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

In yet another embodiment of the invention, antisense or sense oligonucleotides comprising a single-stranded nucleic acid sequence (either RNA or DNA) capable of binding to a target mRNA sequence (forming a duplex) or to the sequence in the double-stranded DNA helix (forming a triple helix) can be made according to the invention. Antisense or sense oligonucleotides, according to the present invention, comprise a fragment of the coding region of cDNA (SEQ ID NO:1, 2, 3, 4, 5, 6, 13 or 15). Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of complexes that block translation (RNA) or transcription (DNA) by one of several means, including enhanced degradation of the duplexes, premature termination of transcription or translation, or by other means. The antisense oligonucleotides thus can be used to block expression of polypeptides of the invention. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation), but retain sequence specificity to be able to bind to target nucleotide sequences. Other examples of sense or antisense oligonucleotides include those oligonucleotides that are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes can be attached to sense or antisense oligonucleotides to modify binding specificities of the antisense or sense oligonucleotide for the target nucleotide sequence.

Antisense or sense oligonucleotides can be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application U.S. Ser. No. 90/02656).

Alternatively, sense or antisense oligonucleotides also can be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

In yet another embodiment, a sense or an antisense oligonucleotide can be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Another embodiment of the invention relates to therapeutic uses of kinases. Kinases play a central role in cellular signal transduction. As such, alterations in kinase expression and/or activation can have profound effects on a plethora of cellular processes, including, but not limited to, activation or inhibition of cell specific responses, proliferation, and programmed cell death (apoptosis). Over expression of cloned kinases or of catalytically inactive mutants of kinases has been used to identify the role a particular kinase plays in mediating specific signaling events.

Kinase mediated cellular signaling often involves a molecular activation cascade, during which an activated kinase propagates a ligand-receptor mediated signal by specifically phosphorylating target substrates. These substrates can themselves be kinases which become activated following phosphorylation. Alternatively, they can be adaptor molecules that facilitate down stream signaling through protein-protein interaction following phosphorylation. Regardless of the nature of the substrate molecule(s), expressed catalytically active versions of the putative kinases in the invention can be used to identify what substrate(s) were recognized and phosphorylated by the kinase(s) of the invention. As such, these kinases can be used as reagents to identify novel molecules involved in signal transduction pathways.

Knowledge of a particular kinase would enable one to enzymatically label the substrate with $^{32}P$ thereby facilitating identification and also to use the resultant radiolabeled protein or a peptide derived from a certain region of the protein as a substrate probe to identify and isolate specific phosphatases. Phosphatases are enzymes whose function is to remove phosphates from selected phosphoproteins; they perform the reverse function of kinases.

In some systems specific glycosylations with N-acetyl glucosamine residues have been described as a biological counter balance to kinases. That is, glycosidases have been suggested to compete with kinases for the same serine or threonine residues to covalently modify. Therefore, the kinase can be used to dissect dynamic interactions between kinase and phosphatase, and also between kinase and glycosidase, and finally to examine the dynamic interactions among kinase, phosphatase and glycosidase together.

Kinases phosphorylate target serine, threonine or tyrosine residues in the context of specific recognition motifs. Recognition motifs can consist solely of primary structure or in some cases recognition requires more complex structural features. One can take advantage of kinases with strict primary sequence recognition requirements by using them as a general labeling reagent. Nucleotides coding for the amino acids recognized by a particular kinase could be engineered onto either end of a protein on interest, thereby "tagging" the molecule. The expressed, tagged protein could be $^{32}P$-labeled at a known site on the engineered tag by its specific kinase, thus generating a well defined, radiolabeled protein.

Because kinases are phosphotransferases, they must take part in protein-protein interactions with at least one or more substrate molecules, i.e. its phosphate recipient(s). Therefore, kinases or polypeptides comprised of portions of a kinase could be used as "baits" in the yeast two hybrid system by well established molecular biology techniques, to identify molecules that interact directly with the polypeptide.

Alternatively, polypeptides of the invention could be engineered prior to expression with a tag such as poly-His or FLAG, then be expressed and purified using either nickel chelate chromatography or anti-FLAG antibody coupled to a resin, respectively. Once bound to the resin, the polypeptide of the invention could be covalently attached using a bifunctional cross-linking agent using well established techniques. The covalently bound polypeptide to the resin could then be used to purify molecules from cell lysates or cell supernatants (following treatment with various reagent) through their affinity for the polypeptide of the invention.

Isolated and purified kinase polypeptides or a fragment thereof of the invention can also be useful as a therapeutic agent in inhibiting signaling. Polypeptides are introduced into the intracellular environment by well-known means, such as by encasing the protein in liposomes or coupling it to a monoclonal antibody targeted to a specific cell type.

DNA, polypeptides, and antibodies against polypeptides of the invention can be used as reagents in a variety of research protocols. A sample of such research protocols are given in Sambrook et al. *Molecular Cloning: A Laboratory Manual*, 2 ed. Vol. 1–3, Cold Spring Harbor Laboratory Press, (1989). For example, these reagents can serve as markers for cell specific or tissue specific expression of RNA or proteins. Similarly, these reagents can be used to investigate constitutive and transient expression of RNA or polypeptides. The DNA can be used to determine the chromosomal location of DNA and to map genes in relation to this chromosomal location. The DNA can also be used to examine genetic heterogeneity and heredity through the use of techniques such as genetic fingerprinting, as well as to identify risks associated with genetic disorders. The DNA can be further used to identify additional genes related to the DNA and to establish evolutionary trees based on the comparison of sequences. The DNA and polypeptides can be used to select for those genes or proteins that are homologous to the DNA or polypeptides, through positive screening procedures such as Southern blotting and immunoblotting and through negative screening procedures such as subtraction.

The polypeptides and fragments of the invention can also be used as a reagent to identify (a) any protein that polypeptide regulates, and (b) other proteins with which it might interact. Polypeptides could be used by coupling recombinant protein to an affinity matrix, or by using them as a bait in the 2-hybrid system. The polypeptides and fragments thereof can be used as reagents in the study of the kinase signaling pathway as a reagent to block kinase signaling.

A hallmark of protein kinases is their ability to phosphorylate other proteins and to auto-phosphorylate. Therefore, in one aspect of the invention, the isolated polypeptides with kinase activity can be used in assays to phosphorylate target proteins, radiolabel target proteins with $^{32}P$, and identify proteins having phosphatase activity. Exemplary methods of phosphorylation assays set forth above are disclosed in U.S. Pat. No. 5,447,860 which is incorporated herein by reference. In addition to full length polypeptides, the invention also includes the isolated active kinase domains of kinases, such as the intracellular domain of transmembrane bound kinases and the cytoplasmic kinases, which can function as reagents in kinase assays. Further, soluble forms of the extracellular domains of the kinases are useful in inhibiting the natural ligand-receptor interaction.

When used as a therapeutic agent, polypeptides of the invention can be formulated into pharmaceutical compositions according to known methods. The polypeptides can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain the polypeptides complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of polypeptides of the invention.

The dosage of the composition can be readily determined by those of ordinary skill in the art. The amount to be administered and the frequency of administration can be determined empirically and will take into consideration the age and size of the patient being treated, as well as the malady being treated.

Treatment comprises administering the composition by any method familiar to those of ordinary skill in the art, including intravenous, intraperitoneal, intracorporeal injection, intra-articular, intraventricular, intrathecal, intramuscular, subcutaneous, topically, tonsillar, intranasally, intravaginally, and orally. The composition may also be given locally, such as by injection into the particular area, either intramuscularly or subcutaneously.

Within the therapeutic and research aspects of the invention, polypeptides of the invention, and peptides based on the amino acid sequence thereof, can be utilized to prepare antibodies that specifically bind to the polypeptides. The term "antibodies" is meant to include polyclonal antibodies, monoclonal antibodies, fragments thereof such as F(ab')2, and Fab fragments, as well as any recombinantly produced binding partners. Antibodies are defined to be specifically binding if they bind polypeptides of the invention with a $K_a$ of greater than or equal to about $10^7$ $M^{-1}$. Affinities of binding partners or antibodies can be readily determined using conventional techniques, for example those described by Scatchard et al., Ann. N.Y Acad. Sci., 51:660 (1949).

Polyclonal antibodies can be readily generated from a variety of sources, for example, horses, cows, goats, sheep, dogs, chickens, rabbits, mice, or rats, using procedures that are well-known in the art. In general, purified polypeptides of the invention, or a peptide based on the amino acid sequence of polypeptides of the invention that is appropriately conjugated, is administered to the host animal typically through parenteral injection. The immunogenicity of these polypeptides can be enhanced through the use of an adjuvant, for example, Freund's complete or incomplete adjuvant. Following booster immunizations, small samples of serum are collected and tested for reactivity to the polypeptides. Examples of various assays useful for such determination include those described in: *Antibodies: A Laboratory Manual*, Harlow and Lane (eds.), Cold Spring Harbor Laboratory Press, 1988; as well as procedures such as countercurrent immuno-electrophoresis (CIEP), radioimmunoassay, radio-immunoprecipitation, enzyme-linked immuno-sorbent assays (ELISA), dot blot assays, and sandwich assays, see U.S. Pat. Nos. 4,376,110 and 4,486,530.

Monoclonal antibodies can be readily prepared using well-known procedures, see for example, the procedures described in U.S. Pat. Nos. 32,011, 4,902,614, 4,543,439, and 4,411,993; RE Monoclonal Antibodies, Hybridomas: *A New Dimension in Biological Analyses*, Plenum Press, Kennett, McKearn, and Bechtol (eds.), 1980. Briefly, the host animals, such as Balb/c mice are injected intraperitoneally at least once, and preferably at least twice at about 3 week intervals with isolated and purified polypeptides or conjugated polypeptides of the invention, optionally in the presence of adjuvant. 10 $\mu$g of isolated and purified polypeptide of the invention or peptides based on the amino acid sequence of polypeptides of the invention in the presence of RIBI adjuvant (RIBI Corp., Hamilton, Mont.). Mouse sera are then assayed by conventional dot blot technique or antibody capture (ABC) to determine which animal produces the highest level of antibody and whose spleen cells are the best candidate for fusion. Approximately two to three weeks later, the mice are given an intravenous boost of the polypeptides or conjugated polypeptides such as 3 $\mu$g suspended in sterile PBS. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG) or more preferably, 50% PEG: 10% DMSO (Sigma). Fusion is plated out into, for example, twenty 96-well flat bottom plates (Corning) containing an appropriate medium, such as HAT supplemented DMEM media and allowed to grow for eight days. Supernatants from resultant hybridomas are collected and added to, for example, a 96-well plate for 60 minutes that is first coated with goat anti-mouse Ig. Following washes, $^{125}$I-polypeptide or peptides of the invention are added to each well, incubated for 60 minutes at room temperature, and washed four times. Positive wells can be subsequently detected by conventional methods, such as autoradiography at −70° C. using Kodak X-Omat S film. Positive clones can be grown in bulk culture and supernatants are subsequently purified, such as over a Protein A column (Pharmacia). It is understood of course that many techniques could be used to generate antibodies against polypeptides and fragmented peptides of the invention and that this embodiment in no way limits the scope of the invention.

The monoclonal antibodies of the invention can be produced using alternative techniques, such as those described by Alting-Mees et al., "Monoclonal Antibody Expression Libraries: A Rapid Alternative to Hybridomas", *Strategies in Molecular Biology* 3:1–9 (1990), which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7:394 (1989).

Other types of "antibodies" can be produced using the information provided herein in conjunction with the state of knowledge in the art. For example, antibodies that have been engineered to contain elements of human antibodies that are capable of specifically binding polypeptides of the invention are also encompassed by the invention.

Once isolated and purified, the antibodies against polypeptides of the invention can be used to detect the presence of the polypeptides in a sample using established assay protocols. Further, the antibodies of the invention can be used therapeutically or for research purposes to bind to the polypeptides and inhibit its activity in vivo or in vitro.

Antibodies immunoreactive with polypeptides of the invention, and in particular, monoclonal antibodies against these polypeptides, are now made available through the invention. Such antibodies can be useful for inhibiting polypeptide activity in vivo and for detecting the presence of polypeptides of the invention in a sample.

In another embodiment, antibodies generated against a polypeptide and fragmented peptides of the invention can be used in combination with polypeptide or fragmented peptide molecular weight markers of the invention to enhance the accuracy in the use of these molecular weight markers to determine the apparent molecular weight and isoelectric point of a sample protein. Polypeptide or fragmented peptide molecular weight markers of the invention can be mixed with a molar excess of a sample protein and the mixture can be resolved by two dimensional electrophoresis by conventional means. Polypeptides can be transferred to a suitable protein binding membrane, such as nitrocellulose, by conventional means and detected by the antibodies of the invention.

The purified polypeptides according to the invention will facilitate the discovery of inhibitors of such polypeptides. The use of a purified polypeptide of the invention in the screening of potential inhibitors thereof is important and can eliminate or reduce the possibility of interfering reactions with contaminants.

In addition, polypeptides of the invention can be used for structure-based design of polypeptide-inhibitors. Such structure-based design is also known as "rational drug design." The polypeptides can be three-dimensionally analyzed by, for example, X-ray crystallography, nuclear magnetic resonance or homology modeling, all of which are well-known methods. The use of the polypeptide structural information in molecular modeling software systems to assist in inhibitor design and inhibitor- polypeptide interaction is also encompassed by the invention. Such computer-assisted modeling and drug design can utilize information such as chemical conformational analysis, electrostatic potential of the molecules, protein folding, etc. For example, most of the design of class-specific inhibitors of metalloproteases has focused on attempts to chelate or bind the catalytic zinc atom. Synthetic inhibitors are usually designed to contain a negatively-charged moiety to which is attached a series of other groups designed to fit the specificity pockets of the particular protease. A particular method of the invention comprises analyzing the three dimensional structure of polypeptides of the invention for likely binding sites of substrates, synthesizing a new molecule that incorporates a predictive reactive site, and assaying the new molecule as described above.

The polypeptides of the present invention may also be used in a screening assay to identify compounds and small molecules which inhibit (antagonize) or enhance (agonize) activation of the polypeptides of the instant invention. Thus, for example, polypeptides of the invention may be used to identify antagonists and agonists from cells, cell-free preparations, chemical libraries, and natural product mixtures. The antagonists and agonists may be natural or modified substrates, ligands, enzymes, receptors, etc. of the polypeptides of the instant invention, or may be structural or functional mimetics of the polypeptides. Potential antagonists of the polypeptides of the instant invention may include small molecules, peptides, and antibodies that bind to and occupy a binding site of the polypeptides, causing them to be unavailable to bind to their ligands and therefore preventing normal biological activity. Other potential antagonists are antisense molecules which may hybridize to mRNA in vivo and block translation of the mRNA into the polypeptides of the instant invention. Potential agonists include small molecules, peptides and antibodies which bind to the instant polypeptides and elicit the same or enhanced biological effects as those caused by the binding of the polypeptides of the instant invention.

Small molecule agonists and antagonists are usually less than 10 K molecular weight and may possess a number of physiochemical and pharmacological properties that enhance cell penetration, resist degradation and prolong their physiological half-lives. (Gibbs, J., Pharmaceutical Research in Molecular Oncology, *Cell*, Vol. 79 (1994).) Antibodies, which include intact molecules as well as fragments such as Fab and F(ab')2 fragments, may be used to bind to and inhibit the polypeptides of the instant invention by blocking the commencement of a signaling cascade. It is preferable that the antibodies are humanized, and more preferable that the antibodies are human. The antibodies of the present invention may be prepared by any of a variety of well-known methods.

Specific screening methods are known in the art and many are extensively incorporated in high throughput test systems so that large numbers of test compounds can be screened within a short amount of time. The assays can be performed in a variety of formats, including protein-protein binding assays, biochemical screening assays, immunoassays, cell based assays, etc. These assay formats are well known in the art. The screening assays of the present invention are amenable to screening of chemical libraries and are suitable for the identification of small molecule drug candidates, antibodies, peptides and other antagonists and agonists.

One embodiment of a method for identifying molecules which antagonize or inhibit the polypeptides involves adding a candidate molecule to a medium which contains cells that express the polypeptides of the instant invention; changing the conditions of said medium so that, but for the presence of the candidate molecule, the polypeptides would be bound to their ligands; and observing the binding and stimulation or inhibition of a functional response. The activity of the cells which were contacted with the candidate molecule may then be compared with the identical cells which were not contacted and agonists and antagonists of the polypeptides of the instant invention may be identified. The measurement of biological activity may be performed by a number of well-known methods such as measuring the amount of protein present (e.g. an ELISA) or of the protein's activity. A decrease in biological stimulation or activation would indicate an antagonist. An increase would indicate an agonist. Specifically, one embodiment of the instant invention includes agonists and antagonists of QQ335 1, SS1771, SS1771A and truncated QQ3351.

Screening assays can further be designed to find molecules that mimic the biological activity of the polypeptides of the instant invention. Molecules which mimic the biological activity of a polypeptide may be useful for enhancing the biological activity of the polypeptide. To identify compounds for therapeutically active agents that mimic the biological activity of a polypeptide, it must first be determined whether a candidate molecule binds to the polypeptide. A binding candidate molecule is then added to a biological assay to determine its biological effects. The biological effects of the candidate molecule are then compared to the those of the polypeptide.

The specification is most thoroughly understood in light of the teachings of the references cited within the specification, which are hereby incorporated by reference. The embodiments within the specification provide an illustration of embodiments of the invention and should not be construed to limit the scope of the invention. The skilled artisan recognizes many other embodiments are encompassed by the claimed invention.

What is claimed is:

1. An isolated polynucleotide molecule comprising the sequence of SEQ ID NO:5 or of SEQ ID NO:13.

2. An isolated polynucleotide molecule encoding an amino acid sequence comprising the sequence of SEQ ID NO:11, or of SEQ ID NO:14, or of Leu-2 through Val-505 of SEQ ID NO:11.

3. A recombinant vector that directs the expression of the polynucleotide molecule of claim 2.

4. An isolated polypeptide having kinase activity encoded by the polynucleotide molecule of claim 1.

5. An isolated polypeptide according to claim 4 having a molecular weight of approximately 58,001 Daltons as determined by SDS-PAGE.

6. An isolated polypeptide according to claim 4 in non-glycosylated form.

7. A recombinant host cell comprising the polynucleotide of claim 2.

8. A method for the production of a polypeptide encoded by the polynucleotide of claim 2 comprising culturing a recombinant host cell comprising the polynucleotide of claim 2 under conditions promoting expression of said polypeptide.

9. The method of claim 8, wherein the host cell is selected from the group consisting of bacterial cells, yeast cells, plant cells, insect cells, and animal cells.

10. An isolated polypeptide having kinase activity produced by the method of claim 8.

11. An isolated polypeptide having kinase activity comprising an amino acid sequence selected from the group consisting of SEQ ID NO:11, SEQ ID NO:14, and the amino acid sequence of Leu-2 through Val-505 of SEQ ID NO:11.

12. The polypeptide of claim 11 comprising the amino acid sequence of SEQ ID NO:14.

13. The polypeptide of claim 11 comprising the amino acid sequence of Leu-2 through Val-505 of SEQ ID NO:11.

14. An isolated polynucleotide molecule comprising the sequence of SEQ ID NO:6 or of SEQ ID NO:15.

15. An isolated polynucleotide molecule encoding an amino acid sequence comprising the sequence of SEQ ID NO:12 or of Pro-2 through Glu-499 of SEQ ID NO:12.

16. A recombinant vector that directs the expression of the polynucleotide molecule of claim 15.

17. An isolated polypeptide having kinase activity encoded by the polynucleotide molecule of claim 14.

18. An isolated polypeptide according to claim 17 having a molecular weight of approximately 57,381 or 67,331 Daltons as determined by SDS-PAGE.

19. An isolated polypeptide according to claim 17 in non-glycosylated form.

20. A recombinant host cell comprising the polynucleotide of claim 15.

21. A method for the production of a polypeptide encoded by the polynucleotide of claim 15 comprising culturing a recombinant host cell comprising the polynucleotide of claim 15 under conditions promoting expression of said polypeptide.

22. The method of claim 21, wherein the host cell is selected from the group consisting of bacterial cells, yeast cells, plant cells, insect cells, and animal cells.

23. An isolated polypeptide having kinase activity produced by the method of claim 21.

24. An isolated polypeptide having kinase activity comprising the amino acid sequence of Pro-2 through Glu-499 of SEQ ID NO:12.

* * * * *

SEQUENCE LISTING

<160> NUMBER OF SEQ ID NOS: 16

<210> SEQ ID NO 1
<211> LENGTH: 181
<212> TYPE: DNA
<213> ORGANISM: Homo sapiens

<400> SEQUENCE: 1

```
gtacgccatg aagtgctgc gcaaggcggc gctggtgcag cgcgccaaga cgcaagagca        60
cacgcgcacc gagcgctcgg tgctggagct ggtgcgccag gcgcccttcc tggtcacgct       120
gcactacgct ttccagacgg atgccaagct gcacctcatc ctggactatg tgagcggcgg       180
g                                                                      181
```

<210> SEQ ID NO 2
<211> LENGTH: 221
<212> TYPE: DNA
<213> ORGANISM: Homo sapiens

<400> SEQUENCE: 2

```
cccgagaggt gccacatcag accgcctccg acttcgtgcg ggactcggcg gccagccacc        60
aggcggagcc cgaggcgtac gagcggcgcg tgtgcttcct gcttctgcaa ctctgcaacg       120
ggctggagca cctgaaggag cacgggatca tccaccggga cctgtgcctg gagaacctgc       180
tgctggtgca ctgcaccctc caggccggcc ccgggcccgc c                           221
```

<210> SEQ ID NO 3
<211> LENGTH: 1085
<212> TYPE: DNA
<213> ORGANISM: Homo sapiens

<400> SEQUENCE: 3

```
cgggcagggc tggagctggg ctgggatccc gagctcggca gcagcgcagc gggccggccc        60
acctgctggt gccctggagg ctctgagccc cggcggcgcc cgggcccacg cggaacgacg       120
gggcgagatg cgagccaccc ctctggctgc tcctgcgggt tccctgtcca ggaagaagcg       180
gttggagttg gatgacaact tagataccga gcgtcccgtc cagaaacgag ctcgaagtgg       240
gccccagccc agactgcccc cctgcctgtt gccctgagc ccacctactg ctccagatcg       300
tgcaactgct gtggccactg cctcccgtct tgggccctat gtcctcctgg agcccgagga       360
gggcgggcgg gcctaccagg ccctgcactg ccctacaggc actgagtata cctgcaaggt       420
```

```
gtacccegtc caggaagccc tggccgtgct ggagccctac gcgcggctgc cccgcacaa      480 gcatgtggct cggcccactg aggtcctggc tggtacccag ctcctctacg ccttttcac     540 tcggacccat ggggacatgc acagcctggt gcgaagccgc caccgtatcc ctgagcctga    600
ggctgccgtg ctcttccgcc agatggccac cgccctggcg cactgtcacc agcacggtct    660
ggtcctgcgt gatctcaagc tgtgtcgctt tgtcttcgct gaccgtgaga ggaagaagct    720
ggtgctggag aacctggagg actcctgcgt gctgactggg ccagatgatt ccctgtggga    780
caagcacgcg tgcccagcct acgtgggacc tgagatactc agctcacggg cctcatactc    840
gggcaaggca gccgatgtct ggagcctggg cgtggcgctc ttcaccatgc tggccggcca    900 ctacccttc caggactcgg agcctgtcct gctcttcggc aagatccgcc gcggggccta    960
cgccttgcct gcaggcctct cggccctgc ccgctgtctg gttcgctgcc tccttcgtcg    1020
ggagccagct gaacggctca cagccacagg catcctcctg caccctggc tgcgacagga    1080 cccga                                                                1085

<210> SEQ ID NO 4
<211> LENGTH: 388
<212> TYPE: DNA
<213> ORGANISM: Homo sapiens

<400> SEQUENCE: 4
cagcgagaag ccgacatgca tcgcctcttc aatcacccca acatccttcg cctcgtggct    60
tactgtctga gggaacgggg tgctaagcat gaggcctggc tgctgctacc attcttcaag    120
agaggtacgc tgtggaatga gatagaaagg ctgaaggaca aagcaacttc ctgaccgag     180 gatcaaatcc tttggctgct gctggggatc tgcagaggcc ttgaggccat tcatgccaag    240
ggttatgcct acagagactt gaagcccacc aatatattgc ttggagatga ggggcagcca    300
gttttaatgg acttgggttc catgaatcaa gcatgcatcc atgtggaggg ctcccgccag    360
gctctgaccc tgcaggactg ggcagccc                                       388

<210> SEQ ID NO 5
<211> LENGTH: 1555
<212> TYPE: DNA
<213> ORGANISM: Homo sapiens

<400> SEQUENCE: 5
atgctaacta gtttaaacag atcttggaac gagacgacct gctgtggaag agcgagcttt    60
ttggaactgt gcacgggaca gattggacgc acacccctcg ggaggcgcga aggcatggaa    120
aatttgaagc atattatcac ccttggccag gtcatccaca aacggtgtga agagatgaaa    180
tactgcaaga acagtgccg gcgcctgggc caccgcgtcc tcggcctgat caagcctctg    240
gagatgctcc aggaccaagg aaagaggagc gtgccctctg agaagttaac cacagccatg    300
aaccgcttca ggctgccct ggaggaggct aatggggaga tagaaaagtt cagcaataga    360
tccaatatct gcaggttct aacagcaagc caggacaaaa tactcttcaa ggacgtgaac    420
aggaagctga gtgatgtctg gaaggagctc tcgctgttac ttcaggttga gcaacgcatg    480 cctgttcac ccataagcca aggagcgtcc tgggcacagg aagatcagca ggatgcagac    540
gaagacaggc gagctttcca gatgctaaga agagataatg aaaaaataga agcttcactg    600
agacgattag aaatcaacat gaaagaaatc aaggaaactt tgaggcagta tttaccacca    660
aaatgcatgc aggagatccc gcaagagcaa atcaaggaga tcaagaagga gcagctttca    720
```

-continued

| | |
|---|---|
| ggatccccgt ggattctgct aagggaaaat gaagtcagca cactttataa aggagaatac | 780 |
| cacagagctc cagtggccat aaaagtattc aaaaaactcc aggctggcag cattgcaata | 840 |
| gtgaggcaga ctttcaataa ggagatcaaa accatgaaga aattcgaatc tcccaacatc | 900 |
| ctgcgtatat ttgggatttg cattgatgaa acagtgactc cgcctcaatt ctccattgtc | 960 |
| atggagtact gtgaactcgg gaccctgagg gagctgttgg atagggaaaa agacctcaca | 1020 |
| cttggcaagc gcatggtcct agtcctgggg gcagcccgag cctataccg gctacaccat | 1080 |
| tcagaagcac ctgaactcca cggaaaaatc agaagctcaa acttcctggt aactcaaggc | 1140 |
| taccaagtga agcttgcagg atttgagttg aggaaaacac agacttccat gagtttggga | 1200 |
| actacgagag aaaagacaga cagagtcaaa tctacagcat atctctcacc tcaggaactg | 1260 |
| gaagatgtat tttatcaata tgatgtaaag tctgaaatat acagctttgg aatcgtcctc | 1320 |
| tgggaaatcg ccactggaga tatcccgttt caaggctgta attctgagaa gatccgcaag | 1380 |
| ctggtggctg tgaagcggca gcaggagcca ctgggtgaag actgcccttc agagctgcgg | 1440 |
| gagatcattg atgagtgccg ggcagcaggt cgtctcgttc caagatctgt agcggccgcc | 1500 |
| cgggccgtcg acgtttaaac gcgtggccct cgagaggttt ccgatccgg tcgat | 1555 |

<210> SEQ ID NO 6
<211> LENGTH: 1498
<212> TYPE: DNA
<213> ORGANISM: Homo sapiens

<400> SEQUENCE: 6

| | |
|---|---|
| cttcccgctg gacgtggagt acggaggccc agaccggagg tgcccgcctc cgccctaccc | 60 |
| gaagcacctg ctgctgcgca gcaagtcgga gcagtacgac ctggacagcc tgtgcgcagg | 120 |
| catggagcag agcctccgtg cgggccccaa cgagcccgag ggcggcgaca gagccgcaa | 180 |
| aagcgccaag ggggacaaag gcggaaagga taaaaagcag attcagacct ctcccgttcc | 240 |
| cgtccgcaaa aacagcagag acgaagagaa gagagagtca cgcatcaaga gctactcgcc | 300 |
| atacgccttt aagttcttca tggagcagca cgtggagaat gtcatcaaaa cctaccagca | 360 |
| gaaggttaac cggaggctgc agctggagca agaaatggcc aaagctggac tctgtgaagc | 420 |
| tgagcaggag cagatgcgga agatcctcta ccagaaaagg tctaattaca caggttaaa | 480 |
| gagggccaag atggacaagt ctatgtttgt caagatcaaa accctgggga tcggtgcctt | 540 |
| tggagaagtg tgccttgctt gtaaggtgga cactcacgcc ctgtacgcca tgaagaccct | 600 |
| aaggaaaaag gatgtcctga accggaatca ggtggcccac gtcaaggccg agagggacat | 660 |
| cctggccgag gcagacaatg agtgggtggt caaactctac tactccttcc aagacaaaga | 720 |
| cagcctgtac tttgtgatgg actacatccc tggtgggac atgatgagcc tgctgatccg | 780 |
| gatggaggtc ttccctgagc acctggcccg gttctacatc gcagagctga ctttggccat | 840 |
| tgagagtgtc cacaagatgg gcttcatcca ccgagacatc aagcctgata cattttgat | 900 |
| agatctggat ggtcacatta aactcacaga tttcggcctc tgcactgggt tcaggtggac | 960 |
| tcacaattcc aaatattacc agaaagggag ccatgtcaga caggacagca tggagcccag | 1020 |
| cgacctctgg gatgatgtgt ctaactgtcg gtgtggggac aggctgaaga ccctagagca | 1080 |
| gagggcgcgg aagcagcacc agaggtgcct ggcacattca ctggtgggga ctccaaacta | 1140 |
| catcgcaccc gaggtgctcc tccgcaaagg gtacactcaa ctctgtgact ggtggagtgt | 1200 |
| tggagtgatt ctcttcgaga tgctggtggg gcagccgccc tttttggcac ctactcccac | 1260 |
| agaaacccag ctgaaggtga tcaactggga gaacacgctc cacattccag cccaggtgaa | 1320 |

```
gctgagccct gaggccaggg acctcatcac caagctgtgc tgctccgcag accaccgcct   1380
ggggcggaat ggggccgatg acctgaaggc ccacccctac ttcagcgcca ttgacttctc   1440
cagtgacatc cggaagcatc cagcccccta cgttcccacc atcagccacc ccatggag    1498
```

<210> SEQ ID NO 7
<211> LENGTH: 60
<212> TYPE: PRT
<213> ORGANISM: Homo sapiens

<400> SEQUENCE: 7

```
Tyr Ala Met Lys Val Leu Arg Lys Ala Ala Leu Val Gln Arg Ala Lys
  1               5                  10                  15

Thr Gln Glu His Thr Arg Thr Glu Arg Ser Val Leu Glu Leu Val Arg
             20                  25                  30

Gln Ala Pro Phe Leu Val Thr Leu His Tyr Ala Phe Gln Thr Asp Ala
         35                  40                  45

Lys Leu His Leu Ile Leu Asp Tyr Val Ser Gly Gly
     50                  55                  60
```

<210> SEQ ID NO 8
<211> LENGTH: 73
<212> TYPE: PRT
<213> ORGANISM: Homo sapiens

<400> SEQUENCE: 8

```
Arg Glu Val Pro His Gln Thr Ala Ser Asp Phe Val Arg Asp Ser Ala
  1               5                  10                  15

Ala Ser His Gln Ala Glu Pro Glu Ala Tyr Glu Arg Arg Val Cys Phe
             20                  25                  30

Leu Leu Leu Gln Leu Cys Asn Gly Leu Glu His Leu Lys Glu His Gly
         35                  40                  45

Ile Ile His Arg Asp Leu Cys Leu Glu Asn Leu Leu Leu Val His Cys
     50                  55                  60

Thr Leu Gln Ala Gly Pro Gly Pro Ala
 65                  70
```

<210> SEQ ID NO 9
<211> LENGTH: 360
<212> TYPE: PRT
<213> ORGANISM: Homo sapiens

<400> SEQUENCE: 9

```
Gly Gln Gly Trp Ser Trp Ala Gly Ile Pro Ser Ser Ala Ala Ala Gln
  1               5                  10                  15

Arg Ala Gly Pro Pro Ala Gly Ala Leu Glu Ala Leu Ser Pro Gly Gly
             20                  25                  30

Ala Arg Ala His Ala Glu Arg Gly Glu Met Arg Ala Thr Pro Leu
         35                  40                  45

Ala Ala Pro Ala Gly Ser Leu Ser Arg Lys Lys Arg Leu Glu Leu Asp
     50                  55                  60

Asp Asn Leu Asp Thr Glu Arg Pro Val Gln Lys Arg Ala Arg Ser Gly
 65                  70                  75                  80

Pro Gln Pro Arg Leu Pro Pro Cys Leu Leu Pro Leu Ser Pro Thr
                 85                  90                  95

Ala Pro Asp Arg Ala Thr Ala Val Ala Thr Ala Ser Arg Leu Gly Pro
                100                 105                 110
```

-continued

```
Tyr Val Leu Leu Glu Pro Glu Gly Gly Arg Ala Tyr Gln Ala Leu
        115                 120                 125

His Cys Pro Thr Gly Thr Glu Tyr Thr Cys Lys Val Tyr Pro Val Gln
        130                 135                 140

Glu Ala Leu Ala Val Leu Glu Pro Tyr Ala Arg Leu Pro Pro His Lys
145                 150                 155                 160

His Val Ala Arg Pro Thr Glu Val Leu Ala Gly Thr Gln Leu Leu Tyr
                165                 170                 175

Ala Phe Phe Thr Arg Thr His Gly Asp Met His Ser Leu Val Arg Ser
            180                 185                 190

Arg His Arg Ile Pro Glu Pro Glu Ala Ala Val Leu Phe Arg Gln Met
        195                 200                 205

Ala Thr Ala Leu Ala His Cys His Gln His Gly Leu Val Leu Arg Asp
    210                 215                 220

Leu Lys Leu Cys Arg Phe Val Phe Ala Asp Arg Glu Arg Lys Lys Leu
225                 230                 235                 240

Val Leu Glu Asn Leu Glu Asp Ser Cys Val Leu Thr Gly Pro Asp Asp
                245                 250                 255

Ser Leu Trp Asp Lys His Ala Cys Pro Ala Tyr Val Gly Pro Glu Ile
            260                 265                 270

Leu Ser Ser Arg Ala Ser Tyr Ser Gly Lys Ala Ala Asp Val Trp Ser
        275                 280                 285

Leu Gly Val Ala Leu Phe Thr Met Leu Ala Gly His Tyr Pro Phe Gln
    290                 295                 300

Asp Ser Glu Pro Val Leu Leu Phe Gly Lys Ile Arg Arg Gly Ala Tyr
305                 310                 315                 320

Ala Leu Pro Ala Gly Leu Ser Ala Pro Ala Arg Cys Leu Val Arg Cys
                325                 330                 335

Leu Leu Arg Arg Glu Pro Ala Glu Arg Leu Thr Ala Thr Gly Ile Leu
            340                 345                 350

Leu His Pro Trp Leu Arg Gln Asp
        355                 360
```

<210> SEQ ID NO 10
<211> LENGTH: 146
<212> TYPE: PRT
<213> ORGANISM: Homo sapiens
<220> FEATURE:
<221> NAME/KEY: UNSURE
<222> LOCATION: (140)..(140)
<223> OTHER INFORMATION: UNSURE

<400> SEQUENCE: 10

```
Gln Arg Glu Ala Asp Met His Arg Leu Phe Asn His Pro Asn Ile Leu
  1               5                   10                  15

Arg Leu Val Ala Tyr Cys Leu Arg Glu Arg Gly Ala Lys His Glu Ala
                20                  25                  30

Trp Leu Leu Pro Phe Phe Lys Arg Gly Thr Leu Trp Asn Glu Ile
            35                  40                  45

Glu Arg Leu Lys Asp Lys Gly Asn Phe Leu Thr Glu Asp Gln Ile Leu
    50                  55                  60

Trp Leu Leu Leu Gly Ile Cys Arg Gly Leu Glu Ala Ile His Ala Lys
65                  70                  75                  80

Gly Tyr Ala Tyr Arg Asp Leu Lys Pro Thr Asn Ile Leu Leu Gly Asp
                85                  90                  95

Glu Gly Gln Pro Val Leu Met Asp Leu Gly Ser Met Asn Gln Ala Cys
```

-continued

```
                    100                 105                 110
Ile His Val Glu Gly Ser Arg Gln Ala Leu Thr Leu Gln Asp Trp Ala
        115                 120                 125

Ala Gln Arg Cys Thr Ile Ser Tyr Arg Ala Pro Xaa Leu Phe Ser Val
    130                 135                 140

Gln Ser
145

<210> SEQ ID NO 11
<211> LENGTH: 505
<212> TYPE: PRT
<213> ORGANISM: Homo sapiens

<400> SEQUENCE: 11

Met Leu Thr Ser Leu Asn Arg Ser Trp Asn Glu Thr Cys Cys Gly
1               5                   10                  15

Arg Ala Ser Phe Leu Glu Leu Cys Thr Gly Gln Ile Gly Arg Thr Pro
                20                  25                  30

Leu Gly Arg Arg Glu Gly Met Glu Asn Leu Lys His Ile Ile Thr Leu
            35                  40                  45

Gly Gln Val Ile His Lys Arg Cys Glu Glu Met Lys Tyr Cys Lys Lys
        50                  55                  60

Gln Cys Arg Arg Leu Gly His Arg Val Leu Gly Leu Ile Lys Pro Leu
65                  70                  75                  80

Glu Met Leu Gln Asp Gln Gly Lys Arg Ser Val Pro Ser Glu Lys Leu
                85                  90                  95

Thr Thr Ala Met Asn Arg Phe Lys Ala Ala Leu Glu Glu Ala Asn Gly
            100                 105                 110

Glu Ile Glu Lys Phe Ser Asn Arg Ser Asn Ile Cys Arg Phe Leu Thr
        115                 120                 125

Ala Ser Gln Asp Lys Ile Leu Phe Lys Asp Val Asn Arg Lys Leu Ser
    130                 135                 140

Asp Val Trp Lys Glu Leu Ser Leu Leu Leu Gln Val Glu Gln Arg Met
145                 150                 155                 160

Pro Val Ser Pro Ile Ser Gln Gly Ala Ser Trp Ala Gln Glu Asp Gln
                165                 170                 175

Gln Asp Ala Asp Glu Asp Arg Arg Ala Phe Gln Met Leu Arg Arg Asp
            180                 185                 190

Asn Glu Lys Ile Glu Ala Ser Leu Arg Arg Leu Glu Ile Asn Met Lys
        195                 200                 205

Glu Ile Lys Glu Thr Leu Arg Gln Tyr Leu Pro Pro Lys Cys Met Gln
    210                 215                 220

Glu Ile Pro Gln Glu Gln Ile Lys Glu Ile Lys Lys Glu Gln Leu Ser
225                 230                 235                 240

Gly Ser Pro Trp Ile Leu Leu Arg Glu Asn Glu Val Ser Thr Leu Tyr
                245                 250                 255

Lys Gly Glu Tyr His Arg Ala Pro Val Ala Ile Lys Val Phe Lys Lys
            260                 265                 270

Leu Gln Ala Gly Ser Ile Ala Ile Val Arg Gln Thr Phe Asn Lys Glu
        275                 280                 285

Ile Lys Thr Met Lys Lys Phe Glu Ser Pro Asn Ile Leu Arg Ile Phe
    290                 295                 300

Gly Ile Cys Ile Asp Glu Thr Val Thr Pro Pro Gln Phe Ser Ile Val
305                 310                 315                 320
```

-continued

```
Met Glu Tyr Cys Glu Leu Gly Thr Leu Arg Glu Leu Asp Arg Glu
            325                 330                 335

Lys Asp Leu Thr Leu Gly Lys Arg Met Val Leu Val Leu Gly Ala Ala
            340                 345                 350

Arg Gly Leu Tyr Arg Leu His His Ser Glu Ala Pro Glu Leu His Gly
            355                 360                 365

Lys Ile Arg Ser Ser Asn Phe Leu Val Thr Gln Gly Tyr Gln Val Lys
370                 375                 380

Leu Ala Gly Phe Glu Leu Arg Lys Thr Gln Thr Ser Met Ser Leu Gly
385                 390                 395                 400

Thr Thr Arg Glu Lys Thr Asp Arg Val Lys Ser Thr Ala Tyr Leu Ser
            405                 410                 415

Pro Gln Glu Leu Glu Asp Val Phe Tyr Gln Tyr Asp Val Lys Ser Glu
            420                 425                 430

Ile Tyr Ser Phe Gly Ile Val Leu Trp Glu Ile Ala Thr Gly Asp Ile
            435                 440                 445

Pro Phe Gln Gly Cys Asn Ser Glu Lys Ile Arg Lys Leu Val Ala Val
            450                 455                 460

Lys Arg Gln Gln Glu Pro Leu Gly Glu Asp Cys Pro Ser Glu Leu Arg
465                 470                 475                 480

Glu Ile Ile Asp Glu Cys Arg Ala Ala Gly Arg Leu Val Pro Arg Ser
            485                 490                 495

Val Ala Ala Arg Ala Val Asp Val
            500                 505

<210> SEQ ID NO 12
<211> LENGTH: 499
<212> TYPE: PRT
<213> ORGANISM: Homo sapiens

<400> SEQUENCE: 12

Phe Pro Leu Asp Val Glu Tyr Gly Gly Pro Asp Arg Arg Cys Pro Pro
1               5                   10                  15

Pro Pro Tyr Pro Lys His Leu Leu Leu Arg Ser Lys Ser Glu Gln Tyr
            20                  25                  30

Asp Leu Asp Ser Leu Cys Ala Gly Met Glu Gln Ser Leu Arg Ala Gly
        35                  40                  45

Pro Asn Glu Pro Glu Gly Gly Asp Lys Ser Arg Lys Ser Ala Lys Gly
    50                  55                  60

Asp Lys Gly Gly Lys Asp Lys Lys Gln Ile Gln Thr Ser Pro Val Pro
65                  70                  75                  80

Val Arg Lys Asn Ser Arg Asp Glu Glu Lys Arg Glu Ser Arg Ile Lys
                85                  90                  95

Ser Tyr Ser Pro Tyr Ala Phe Lys Phe Phe Met Glu Gln His Val Glu
            100                 105                 110

Asn Val Ile Lys Thr Tyr Gln Gln Lys Val Asn Arg Arg Leu Gln Leu
        115                 120                 125

Glu Gln Glu Met Ala Lys Ala Gly Leu Cys Glu Ala Glu Gln Glu Gln
130                 135                 140

Met Arg Lys Ile Leu Tyr Gln Lys Glu Ser Asn Tyr Asn Arg Leu Lys
145                 150                 155                 160

Arg Ala Lys Met Asp Lys Ser Met Phe Val Lys Ile Lys Thr Leu Gly
                165                 170                 175

Ile Gly Ala Phe Gly Glu Val Cys Leu Ala Cys Lys Val Asp Thr His
            180                 185                 190
```

```
Ala Leu Tyr Ala Met Lys Thr Leu Arg Lys Lys Asp Val Leu Asn Arg
            195                 200                 205
Asn Gln Val Ala His Val Lys Ala Glu Arg Asp Ile Leu Ala Glu Ala
        210                 215                 220
Asp Asn Glu Trp Val Val Lys Leu Tyr Tyr Ser Phe Gln Asp Lys Asp
225                 230                 235                 240
Ser Leu Tyr Phe Val Met Asp Tyr Ile Pro Gly Gly Asp Met Met Ser
                245                 250                 255
Leu Leu Ile Arg Met Glu Val Phe Pro Glu His Leu Ala Arg Phe Tyr
            260                 265                 270
Ile Ala Glu Leu Thr Leu Ala Ile Glu Ser Val His Lys Met Gly Phe
        275                 280                 285
Ile His Arg Asp Ile Lys Pro Asp Asn Ile Leu Ile Asp Leu Asp Gly
    290                 295                 300
His Ile Lys Leu Thr Asp Phe Gly Leu Cys Thr Gly Phe Arg Trp Thr
305                 310                 315                 320
His Asn Ser Lys Tyr Tyr Gln Lys Gly Ser His Val Arg Gln Asp Ser
                325                 330                 335
Met Glu Pro Ser Asp Leu Trp Asp Asp Val Ser Asn Cys Arg Cys Gly
            340                 345                 350
Asp Arg Leu Lys Thr Leu Glu Gln Arg Ala Arg Lys Gln His Gln Arg
        355                 360                 365
Cys Leu Ala His Ser Leu Val Gly Thr Pro Asn Tyr Ile Ala Pro Glu
    370                 375                 380
Val Leu Leu Arg Lys Gly Tyr Thr Gln Leu Cys Asp Trp Trp Ser Val
385                 390                 395                 400
Gly Val Ile Leu Phe Glu Met Leu Val Gly Gln Pro Pro Phe Leu Ala
                405                 410                 415
Pro Thr Pro Thr Glu Thr Gln Leu Lys Val Ile Asn Trp Glu Asn Thr
            420                 425                 430
Leu His Ile Pro Ala Gln Val Lys Leu Ser Pro Glu Ala Arg Asp Leu
        435                 440                 445
Ile Thr Lys Leu Cys Cys Ser Ala Asp His Arg Leu Gly Arg Asn Gly
    450                 455                 460
Ala Asp Asp Leu Lys Ala His Pro Phe Phe Ser Ala Ile Asp Phe Ser
465                 470                 475                 480
Ser Asp Ile Arg Lys His Pro Ala Pro Tyr Val Pro Thr Ile Ser His
                485                 490                 495
Pro Met Glu

<210> SEQ ID NO 13
<211> LENGTH: 375
<212> TYPE: DNA
<213> ORGANISM: Homo sapiens

<400> SEQUENCE: 13
cttgcaggat ttgagttgag gaaaacacag acttccatga gtttgggaac tacgagagaa      60
aagacagaca gagtcaaatc tacagcatat ctctcacctc aggaactgga agatgtattt     120
tatcaatatg atgtaaagtc tgaaatatac agctttggaa tcgtcctctg ggaaatcgcc     180
actggagata tcccgtttca aggctgtaat tctgagaaga tccgcaagct ggtggctgtg     240
aagcggcagc aggagccact gggtgaagac tgcccttcag agctgcggga gatcattgat     300
gagtgccggg cccatgatcc ctctgtgcgg ccctctgtgg atgaaatctt aaagaaactc     360
``` tccaccttttt ctaag                                                      375

<210> SEQ ID NO 14
<211> LENGTH: 125
<212> TYPE: PRT
<213> ORGANISM: Homo sapiens

<400> SEQUENCE: 14

Leu Ala Gly Phe Glu Leu Arg Lys Thr Gln Thr Ser Met Ser Leu Gly
 1               5                  10                  15

Thr Thr Arg Glu Lys Thr Asp Arg Val Lys Ser Thr Ala Tyr Leu Ser
            20                  25                  30

Pro Gln Glu Leu Glu Asp Val Phe Tyr Gln Tyr Asp Val Lys Ser Glu
        35                  40                  45

Ile Tyr Ser Phe Gly Ile Val Leu Trp Glu Ile Ala Thr Gly Asp Ile
    50                  55                  60

Pro Phe Gln Gly Cys Asn Ser Glu Lys Ile Arg Lys Leu Val Ala Val
65                  70                  75                  80

Lys Arg Gln Gln Glu Pro Leu Gly Glu Asp Cys Pro Ser Glu Leu Arg
                85                  90                  95

Glu Ile Ile Asp Glu Cys Arg Ala His Asp Pro Ser Val Arg Pro Ser
            100                 105                 110

Val Asp Glu Ile Leu Lys Lys Leu Ser Thr Phe Ser Lys
        115                 120                 125

<210> SEQ ID NO 15
<211> LENGTH: 1961
<212> TYPE: DNA
<213> ORGANISM: Homo sapiens

<400> SEQUENCE: 15
tcccgctgga cgtggagtac ggaggcccag accggaggtg cccgcctccg ccctacccga    60
agcacctgct gctgcgcagc aagtcggagc agtacgacct ggacagcctg tgcgcaggca   120
tggagcagag cctccgtgcg ggccccaacg agcccgaggg cggcgacaag agccgcaaaa   180
gcgccaaggg ggacaaaggc ggaaaggata aaaagcagat tcagacctct cccgttcccg   240
tccgcaaaaa cagcagagac gaagagaaga gagagtcacg catcaagagc tactcgccat   300
acgcctttaa gttcttcatg gagcagcacg tggagaatgt catcaaaacc taccagcaga   360
aggttaaccg gaggctgcag ctggagcaag aaatggccaa agctggactc tgtgaagctg   420
agcaggagca gatgcggaag atcctctacc agaaagagtc taattacaac aggttaaaga   480
gggccaagat ggacaagtct atgtttgtca agatcaaaac cctgggatc ggtgcctttg    540 gagaagtgtg ccttgcttgt aaggtggaca ctcacgccct gtacgccatg aagaccctaa   600
ggaaaaagga tgtcctgaac cggaatcagg tgcccacgt caaggccgag agggacatcc    660 tgccgaggc agacaatgag tgggtggtca aactctacta ctccttccaa gacaaagaca   720
gcctgtactt tgtgatggac tacatccctg gtggggacat gatgagcctg ctgatccgga   780
tggaggtctt ccctgagcac ctggcccggt ctacatcgc agagctgact tggccattg    840 agagtgtcca agatgggc ttcatccacc gagacatcaa gctgataac atttgatag     900 atctggatgg tcacattaaa ctcacagatt tcggcctctg cactgggttc aggtggactc   960
acaattccaa atattaccag aaagggagcc atgtcagaca ggacagcatg gagcccagcg  1020
acctctggga tgatgtgtct aactgtcggt gtggggacag gctgaagacc ctagagcaga  1080

-continued

```
gggcgcggaa gcagcaccag aggtgcctgg cacattcact ggtggggact ccaaactaca     1140
tcgcacccga ggtgctcctc cgcaaagggt acactcaact ctgtgactgg tggagtgttg     1200
gagtgattct cttcgagatg ctggtggggc agccgccctt tttggcacct actcccacag     1260
aaacccagct gaaggtgatc aactgggaga cacgctcca cattccagcc caggtgaagc      1320
tgagccctga ggccagggac ctcatcacca agctgtgctg ctccgcagac caccgcctgg    1380
ggcggaatgg ggccgatgac ctgaaggccc acccttctt cagcgccatt gacttctcca     1440
gtgacatccg gaagcatcca gcccctacg ttcccaccat cagccacccc atggacacct     1500
cgaatttcga ccccgtagat gaagaaagcc cttggaacga tgccagcgaa ggtagcacca    1560
aggcctggga cacactcacc tcgcccaata caagcatcc tgagcacgca ttttacgaat     1620
tcaccttccg aaggttcttt gatgacaatg gctacccctt tcgatgccca aagccttcag    1680
gagcagaagc ttcacaggct gagagctcag atttagaaag ctctgatctg gtggatcaga    1740
ctgaaggctg ccagcctgtg tacgtgtaga tgggggccag gcacccccac cactcgctgc    1800
ctcccaggtc agggtcccgg agccggtgcc ctcacaggcc aatagggaag ccgagggctg    1860
ttttgtttta aattagtccg tcgattactt cacttgaaat tctgctcttc accaagaaaa    1920
cccaaacagg acactttga aaacagcggt gccgcgaatt c                          1961
```

<210> SEQ ID NO 16
<211> LENGTH: 588
<212> TYPE: PRT
<213> ORGANISM: Homo sapiens

<400> SEQUENCE: 16

```
Pro Leu Asp Val Glu Tyr Gly Gly Pro Asp Arg Arg Cys Pro Pro Pro
 1               5                  10                  15

Pro Tyr Pro Lys His Leu Leu Arg Ser Lys Ser Glu Gln Tyr Asp
                20                  25                  30

Leu Asp Ser Leu Cys Ala Gly Met Glu Gln Ser Leu Arg Ala Gly Pro
             35                  40                  45

Asn Glu Pro Glu Gly Gly Asp Lys Ser Arg Lys Ser Ala Lys Gly Asp
         50                  55                  60

Lys Gly Gly Lys Asp Lys Lys Gln Ile Gln Thr Ser Pro Val Pro Val
 65                  70                  75                  80

Arg Lys Asn Ser Arg Asp Glu Glu Lys Arg Glu Ser Arg Ile Lys Ser
                 85                  90                  95

Tyr Ser Pro Tyr Ala Phe Lys Phe Phe Met Glu Gln His Val Glu Asn
                100                 105                 110

Val Ile Lys Thr Tyr Gln Gln Lys Val Asn Arg Arg Leu Gln Leu Glu
            115                 120                 125

Gln Glu Met Ala Lys Ala Gly Leu Cys Glu Ala Glu Gln Glu Gln Met
        130                 135                 140

Arg Lys Ile Leu Tyr Gln Lys Glu Ser Asn Tyr Asn Arg Leu Lys Arg
145                 150                 155                 160

Ala Lys Met Asp Lys Ser Met Phe Val Lys Ile Lys Thr Leu Gly Ile
                165                 170                 175

Gly Ala Phe Gly Glu Val Cys Leu Ala Cys Lys Val Asp Thr His Ala
            180                 185                 190

Leu Tyr Ala Met Lys Thr Leu Arg Lys Lys Asp Val Leu Asn Arg Asn
        195                 200                 205

Gln Val Ala His Val Lys Ala Glu Arg Asp Ile Leu Ala Glu Ala Asp
    210                 215                 220
```

-continued

```
Asn Glu Trp Val Val Lys Leu Tyr Tyr Ser Phe Gln Asp Lys Asp Ser
225                 230                 235                 240

Leu Tyr Phe Val Met Asp Tyr Ile Pro Gly Gly Asp Met Met Ser Leu
            245                 250                 255

Leu Ile Arg Met Glu Val Phe Pro Glu His Leu Ala Arg Phe Tyr Ile
            260                 265                 270

Ala Glu Leu Thr Leu Ala Ile Glu Ser Val His Lys Met Gly Phe Ile
        275                 280                 285

His Arg Asp Ile Lys Pro Asp Asn Ile Leu Ile Asp Leu Asp Gly His
    290                 295                 300

Ile Lys Leu Thr Asp Phe Gly Leu Cys Thr Gly Phe Arg Trp Thr His
305                 310                 315                 320

Asn Ser Lys Tyr Tyr Gln Lys Gly Ser His Val Arg Gln Asp Ser Met
                325                 330                 335

Glu Pro Ser Asp Leu Trp Asp Asp Val Ser Asn Cys Arg Cys Gly Asp
            340                 345                 350

Arg Leu Lys Thr Leu Glu Gln Arg Ala Arg Lys Gln His Gln Arg Cys
        355                 360                 365

Leu Ala His Ser Leu Val Gly Thr Pro Asn Tyr Ile Ala Pro Glu Val
    370                 375                 380

Leu Leu Arg Lys Gly Tyr Thr Gln Leu Cys Asp Trp Trp Ser Val Gly
385                 390                 395                 400

Val Ile Leu Phe Glu Met Leu Val Gly Gln Pro Pro Phe Leu Ala Pro
                405                 410                 415

Thr Pro Thr Glu Thr Gln Leu Lys Val Ile Asn Trp Glu Asn Thr Leu
            420                 425                 430

His Ile Pro Ala Gln Val Lys Leu Ser Pro Glu Ala Arg Asp Leu Ile
        435                 440                 445

Thr Lys Leu Cys Cys Ser Ala Asp His Arg Leu Gly Arg Asn Gly Ala
    450                 455                 460

Asp Asp Leu Lys Ala His Pro Phe Phe Ser Ala Ile Asp Phe Ser Ser
465                 470                 475                 480

Asp Ile Arg Lys His Pro Ala Pro Tyr Val Pro Thr Ile Ser His Pro
                485                 490                 495

Met Asp Thr Ser Asn Phe Asp Pro Val Asp Glu Glu Ser Pro Trp Asn
            500                 505                 510

Asp Ala Ser Glu Gly Ser Thr Lys Ala Trp Asp Thr Leu Thr Ser Pro
        515                 520                 525

Asn Asn Lys His Pro Glu His Ala Phe Tyr Glu Phe Thr Phe Arg Arg
    530                 535                 540

Phe Phe Asp Asp Asn Gly Tyr Pro Phe Arg Cys Pro Lys Pro Ser Gly
545                 550                 555                 560

Ala Glu Ala Ser Gln Ala Glu Ser Ser Asp Leu Glu Ser Ser Asp Leu
                565                 570                 575

Val Asp Gln Thr Glu Gly Cys Gln Pro Val Tyr Val
            580                 585
```